(12) United States Patent
Shamloo et al.

(10) Patent No.: US 9,072,746 B2
(45) Date of Patent: Jul. 7, 2015

(54) METHOD FOR ENHANCING LEARNING AND MEMORY IMPAIRED BY NEURODEGENERATIVE DISORDERS AND COMPOUNDS AND COMPOSITIONS FOR EFFECTING THE SAME

(75) Inventors: Mehrdad Shamloo, Palo Alto, CA (US); Mehrdad Faizi, Palo Alto, CA (US); William Mobley, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/641,987

(22) PCT Filed: Apr. 22, 2011

(86) PCT No.: PCT/US2011/000722
§ 371 (c)(1), (2), (4) Date: Jan. 2, 2013

(87) PCT Pub. No.: WO2011/133226
PCT Pub. Date: Oct. 27, 2011

(65) Prior Publication Data
US 2013/0096126 A1  Apr. 18, 2013

Related U.S. Application Data

(60) Provisional application No. 61/282,924, filed on Apr. 22, 2010.

(51) Int. Cl.
A61K 31/137 (2006.01)
A61K 31/5375 (2006.01)
A61K 31/138 (2006.01)

(52) U.S. Cl.
CPC .......... *A61K 31/5375* (2013.01); *A61K 31/137* (2013.01); *A61K 31/138* (2013.01)

(58) Field of Classification Search
None
See application file for complete search history.

(56) References Cited

U.S. PATENT DOCUMENTS

| 2003/0216413 A1 | 11/2003 | Root-Bernstein et al. |
| 2005/0118286 A1 | 6/2005 | Suffin et al. |
| 2010/0130566 A1 | 5/2010 | Purpura et al. |
| 2013/0053350 A1 | 2/2013 | Colca et al. |

FOREIGN PATENT DOCUMENTS

WO   WO 98/09523   *   3/1998

OTHER PUBLICATIONS

Mehlsen et al. Xamoterol, a new selective beta-1 adrenoceptor partial agonsit, in the treatment of postural hypotension. Acta. Med. Scand. 1986; 219: 173-7.*
Michel et al. The beta1-adrenoceptor agonist xamoterol protects dopaminergic neurons from apoptosis. Society for Neuroscience Abstracts, 1999, vol. 25, No. 1-2, pp. 2018, Oct. 23-28, 1999).*

(Continued)

*Primary Examiner* — Anna Pagonakis
(74) *Attorney, Agent, or Firm* — William E. Beaumont

(57) ABSTRACT

A method for enhancing learning or memory of both in a mammal having impaired learning or memory of both from a neuro-degenerative disorder, which entails the step of administering at least one compound or a salt thereof which is a $\beta_1$-adrenergic receptor agonist, partial agonist or receptor ligand in an amount effective to improve the learning or memory or both of said mammal.

12 Claims, 10 Drawing Sheets

(56) References Cited

OTHER PUBLICATIONS

Kemppainen et al. Hippocampal dopamine D2 receptors correlate with memory functions in Alzheimer's disease. European Journal of Neuroscience, vol. 18, pp. 149-154, 2003.*

Dierssen et al. Alterations of central noradrenergic transmission in Ts65Dn mouse, a model for Down Syndrome. Brain Research, 1997, vol. 749, pp. 238-244.

Murchison et al. A distinct role for epinehprine in memory retrieval. Cell, 2004, vol. 117, pp. 131-143.

* cited by examiner

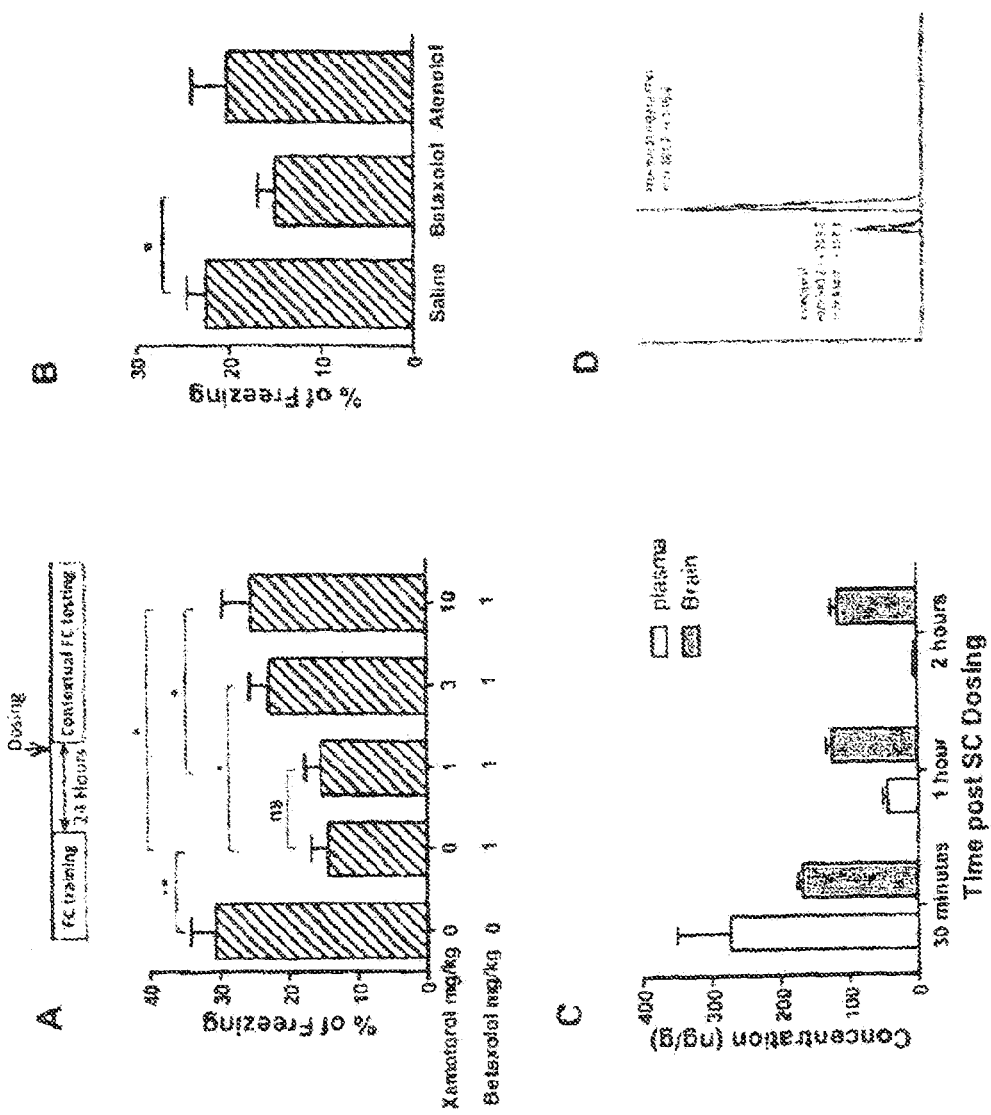

METHOD FOR ENHANCING LEARNING AND MEMORY IMPAIRED BY NEURODEGENERATIVE DISORDERS AND COMPOUNDS AND COMPOSITIONS FOR EFFECTING THE SAME

FIELD OF THE INVENTION

The present invention relates to a method for enhancing learning and memory in mammals, including humans, which have been impaired by neuro-degenerative disorders; and compounds and compositions for effecting this enhancement.

BACKGROUND OF THE INVENTION

Down Syndrome (DS), trisomy of chromosome 21 (HSA21), is the most prevalent form of mental retardation caused by genetic abnormalities in humans (Epstein et al., 1990). Extra copies of all or part of HSA21 affect a number of organs, in particular the central nervous system. In addition to intellectual dysfunction, people with DS may suffer from congenital cardiac disease, immune and endocrine problems, genitourinary defects, gastrointestinal abnormalities, and orofacial malformations (Greenwood and Nadas, 1976; Korenberg et al., 1994; Cleves et al., 2007). An important characteristic of DS is the development of the neuropathological markers of Alzheimer's disease (AD) by age 40 and frequently, in later life, of cognitive decline (Burger and Vogel, 1973; Casanova et al., 1985; Mufson et al., 2002). Ts65Dn mice are the most commonly used mouse model of DS. They are segmentally trisomic for mouse chromosome 16 (MMU16), which is generated by Robertsonian segmental translocation of MMU16 to the MMU17 centromere (Davisson et al., 1990). The chromosomal segment contains an extra copy of more than 104 genes with homologues on HSA21 (Reeves et al., 1995; Baxter et al., 2000; Kahlem et al., 2004). Ts65Dn mice have shorter life expectancies and show morphological, neurological, and structural abnormalities that parallel those in people with DS (Dierssen et al., 1996; Holtzman et al., 1996; Dierssen et al., 1997; Granholm et al., 2000; Belichenko et al., 2004; Lumbreras et al., 2006; Salehi et al., 2006; Salehi et al., 2007). They show changes in the structure and function of neuronal circuits, including deficits in hippocampal synaptic plasticity, as demonstrated in both cellular signaling and electrophysiological studies (Dierssen et al., 1996; Dierssen et al., 1997; Siarey et al., 1997; Siarey et al., 1999; Kleschevnikov et al., 2004; Siarey et al., 2005; Siarey et al., 2006). Ts65Dn mice also share behavioral abnormalities similar to those seen in DS, along with increased locomotor activity (Davisson et al., 1993; Escorihuela et al., 1995; Reeves et al., 1995; Coussons-Read and Crnic, 1996; Stewart et al., 2007). Male trisomic mice show increased repetitive and stereotypical movement in the home cage. Ts65Dn mice have also shown impaired learning and memory, especially in hippocampus-dependent tasks, including the water maze spatial learning task (Escorihuela et al., 1995; Reeves et al., 1995; Demas et al., 1996; Holtzman et al., 1996), context discrimination learning (Hyde et al., 2001a), dry and water radial arm maze tests (Demas et al., 1996, 1998; Bimonte-Nelson et al., 2003; Hunter et al., 2004), and spontaneous alternation (Belichenko et al., 2007; Chang and Gold, 2008). However, in some learning and memory tests, such as passive avoidance, no significant difference was reported (Coussons-Read and Crnic, 1996; Holtzman et al., 1996; Rueda et al., 2008).

Despite the fact that many studies have been conducted and many changes have been noted in this model, No therapeutic treatments or approaches have been developed for this disorder.

SUMMARY OF THE INVENTION

It is an object of the present invention to provide a robust and reproducible behavioral paradigm for the phenotyping of Ts65Dn mice in motor function, learning and memory as well as social behavior.

It is further an object of the present invention to provide a method for identifying effective pharmacological approaches for treating behavioral and cognitive disorders in mammals, particularly humans, with DS and other neuro-degenerative disorders.

Moreover, it is an object of the present invention to provide a method for enhancing learning and memory in mammals, particularly, humans, whose learning and memory have been impaired by neuro-degenerative disorders.

It is also an object of the present invention to provide a method of improving sociability and social memory in mammals, particularly humans, whose sociability and social memory have been impaired by neuro-degenerative disorders.

It is also an object of the present invention to provide a method of behaviorally phenotyping a Ts65Dn mouse model of Down Syndrome for conducting pathogenic studies in humans.

The above objects and others are provided by a method for enhancing learning or memory or both in a mammal having impaired learning or memory or both from a neuro-degenerative disorder, which entails a step of administering at least one compound or a salt thereof, which compound is a $\beta 1$-adrenergic receptor agonist partial agonist or receptor ligand in an amount effective to improve said learning or memory or both of the mammal.

In the 3-chamber sociability test (A), mice spent more time investigating a caged intruder than an empty Cage during session B, n=10 for both 2N and Ts65Dn mice. In the first 5 minute bin of the social novelty 3-chamber test during session C (B), animals spent more time sniffing at a cage with a novel Intruder compared to sniffing a cage with a familiar intruder, N (2N)=9, n (Ts65Dn)=10. In the 2-trial social memory test (C), 30 minutes after the first interaction with an OEF, mice spent the same amount of time exploring both a familiar and a novel OEF intruder, n (2N)=9, n (Ts65Dn)=8. In the first 30 seconds of the 5-trial social memory test (D), Ts65Dn mice displayed no habituation, whereas 2N mice exhibited a significant habituation to the familiar OEF and a significant dishabituation to the novel OEF, N (2N)=9, n (Ts65Dn)=10. Olfactory habituation to social (E) and nonsocial cues (F) presented with cotton-tipped swabs was significant in both genotypes. In panels E and F, n (2N)=10 and n (Ts65Dn)=10. Results are presented as mean±/+SEM (*=$p<0.05$, and =$p<0.01$, *=$p<0.001$, and ns=not significant).

Figure 5:
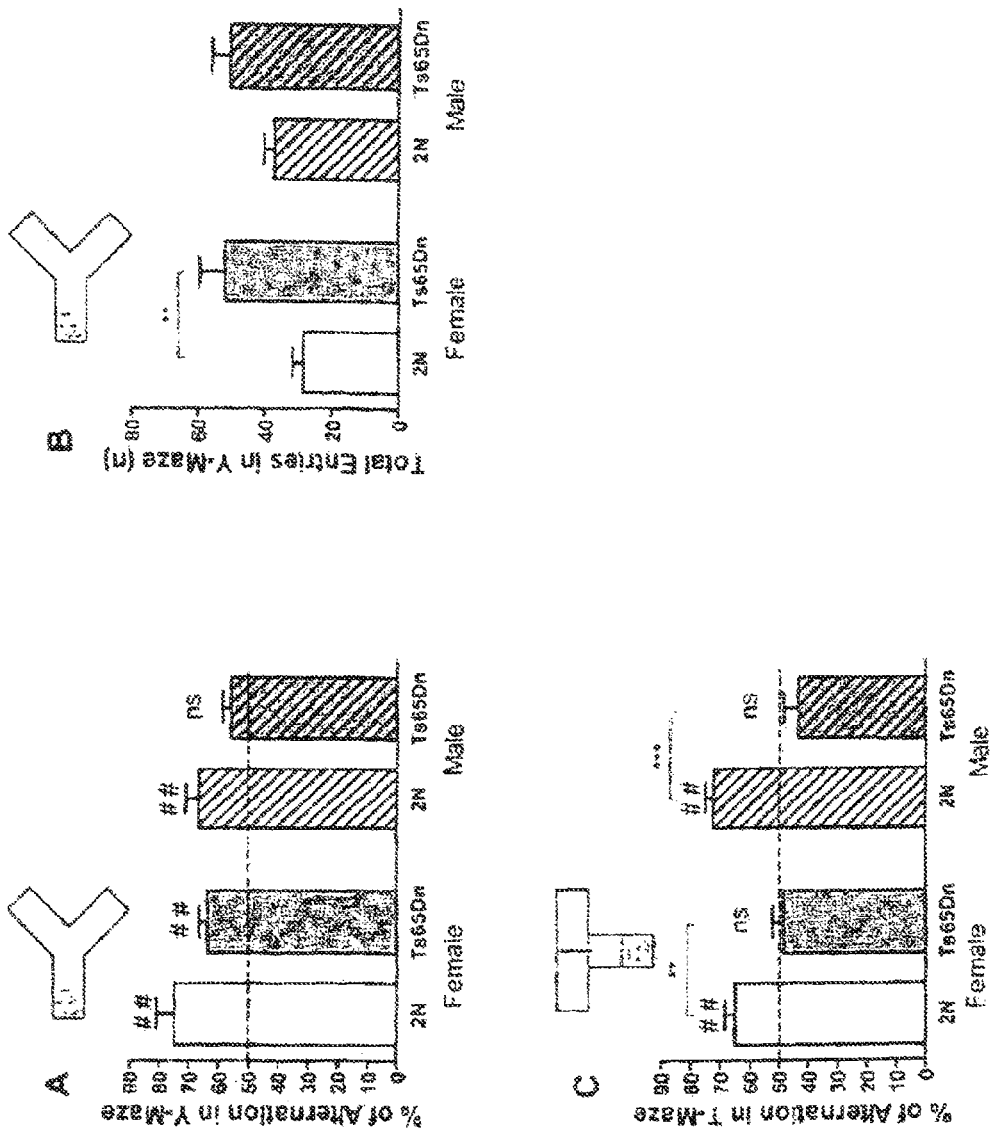

FIG. 5 Y-maze and T-maze spontaneous alternation in male and female Ts65Dn and 2N mice illustrates Y-maze and T-maze spontaneous alternation. Alternation rates in Y-maze in Y-maze (A) and T-maze (C) and total number of entries to arms of Y-maze (B) are presented. In all graphs Mean+SEM of parameters are shown. In the Y-maze study, n=7 for female Ts65Dn mice and n=8 for male Ts65Dn, female 2N, and female Ts65Dn mice. In the T-maze test, n=10 for female 2N mice, n=9 for female Ts65Dn mice, n=6 for male 2N mice, and n=7 for male Ts65Dn mice. Alternation rate in Y-maze and T-maze (A and C) was compared with the chance level (50%) and the significant and non-significant differences are shown (ns=not significant, ##=$p<0.01$ compared to chance level). In addition, the effect of genotype and sex was analyzed and in both the Y-maze and Tmaze, alternation rate in Ts65Dn mice was significantly lower than 2N mice. Within group comparison between each pair of genotypes was analyzed, and only the significant differences are shown (*=$p<0.05$, =$p<0.01$ and *=$p<0.001$).

Figure 6:
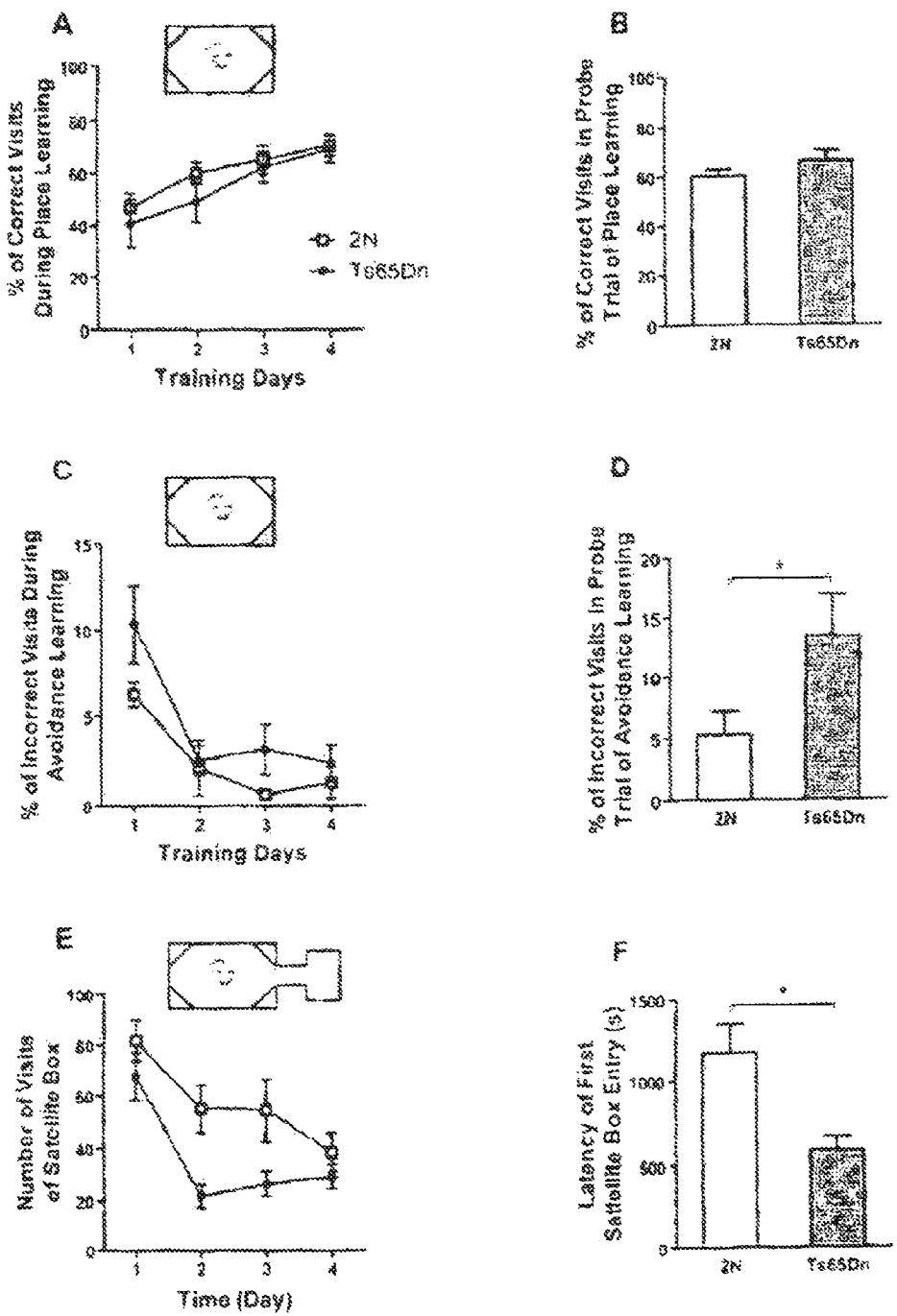

FIG. 6 Place learning, place avoidance, and novelty exploration tests in Intellicage Illustrates place learning, place avoidance and novelty exploration in Intellicage. In the place learning task, percent of correct visits (A) and probe trial after 72 hrs (B) are presented. In both A and B there was no significant effect of genotype. Genotype did not show any effect on percent of incorrect visits during avoidance learning (C), but after 72 hrs retention, Ts65Dn mice had significantly more incorrect visits (D). After adding the satellite box to the Intellicage, the number of visits to the satellite box (E) and latency to the first visit of the box (F) are graphed. Although there is a significant effect of genotype in E, the post hoc test did not show any significant difference between the genotype in each individual time point. In graphs B, D and F, each pair of data was tested and only the significant differences are shown (*=$p<0.05$). Mean/SEM is shown. In A and B, n (2N) =10 and n(Ts65Dn)=7. In C and D, n(2N)=9 and n(Ts65Dn) =6. In E and F, n(2N)=10 and n(Ts65Dn)=6. The experiment was done on female mice.

Figure 7:
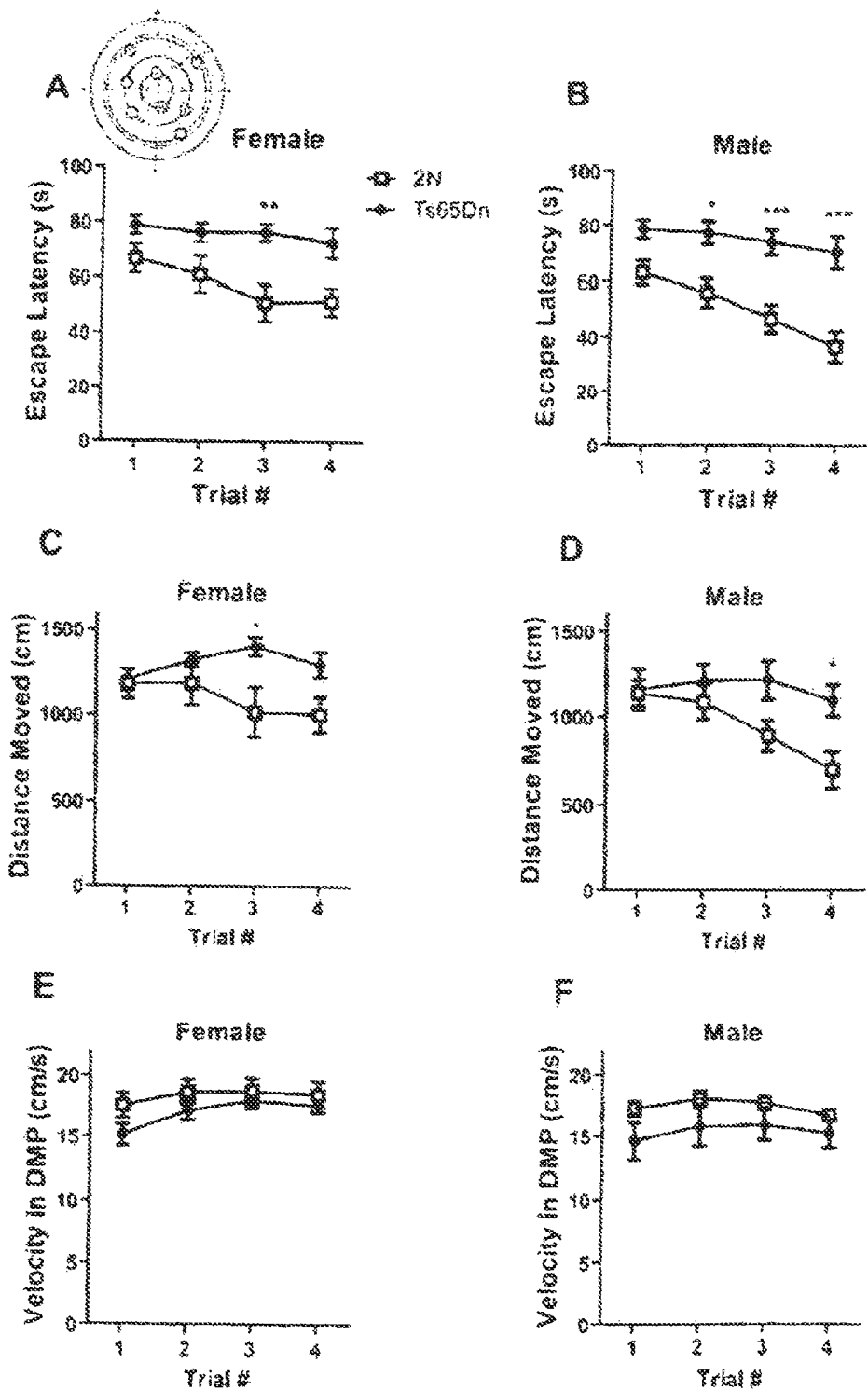

FIG. 7 Delayed matching-to-place water maze task for testing spatial working memory/episodic-like memory Illustrates delayed-matched-to place water maze task for testing spatial working memory/episodic-like memory. Escape latency for female (A) and male (B) mice are presented. In both A and B there was a significant effect of genotype and the results of post hoc analysis for each time point is shown (*–$p<0.05$, =$p<0.01$, and *=$p<0.001$). In all groups, Mean SEM is shown and n=8.

Figure 8:
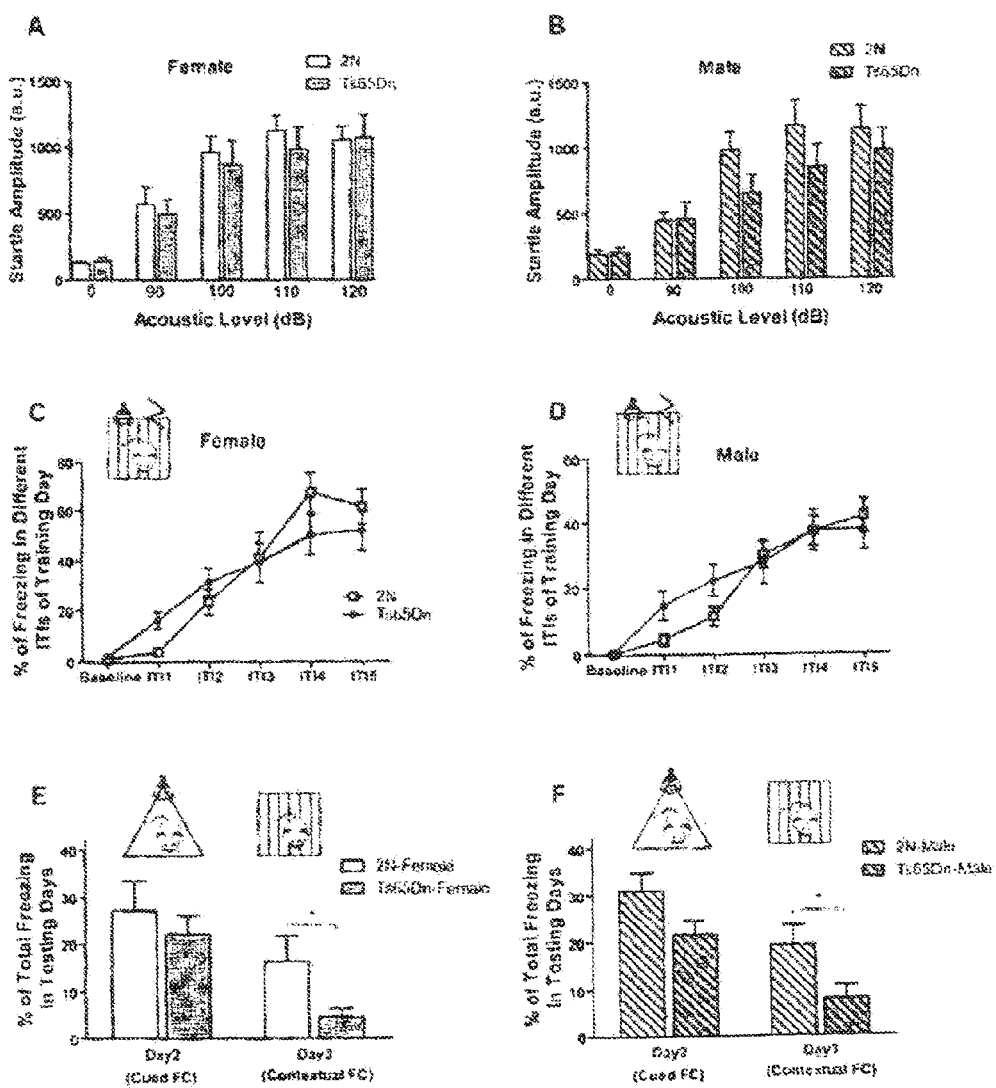

FIG. 8 Fear conditioning and startle response. Illustrates fear conditioning and startle response. Freezing during the training day in different it is and in the baseline period for female (A) and male (B) Ts65Dn mice and 2N controls are presented. In both genders, there was no significant effect of genotype in acquisition of the task. Total freezing in testing days (C and D) indicates that there was no statistically significant difference between genotypes in tone-cued fear conditioning, but in both sexes, Ts65Dn mice showed deficit in contextual fear conditioning. In the fear conditioning test, n=10 for both 2N and Ts65Dn female mice and n=21 for male 2N and n=17 for male Ts65Dn mice (*=$p<0.05$). In the startle response test, no significant effect of genotype was seen in both female (E) and male (F) mice. In the startle response test no significant effect of genotype was seen in both female (E) and male (F) mice. In the startle response test, n=8 for all groups. In all panels Mean/SEM is shown.

Figure 9:
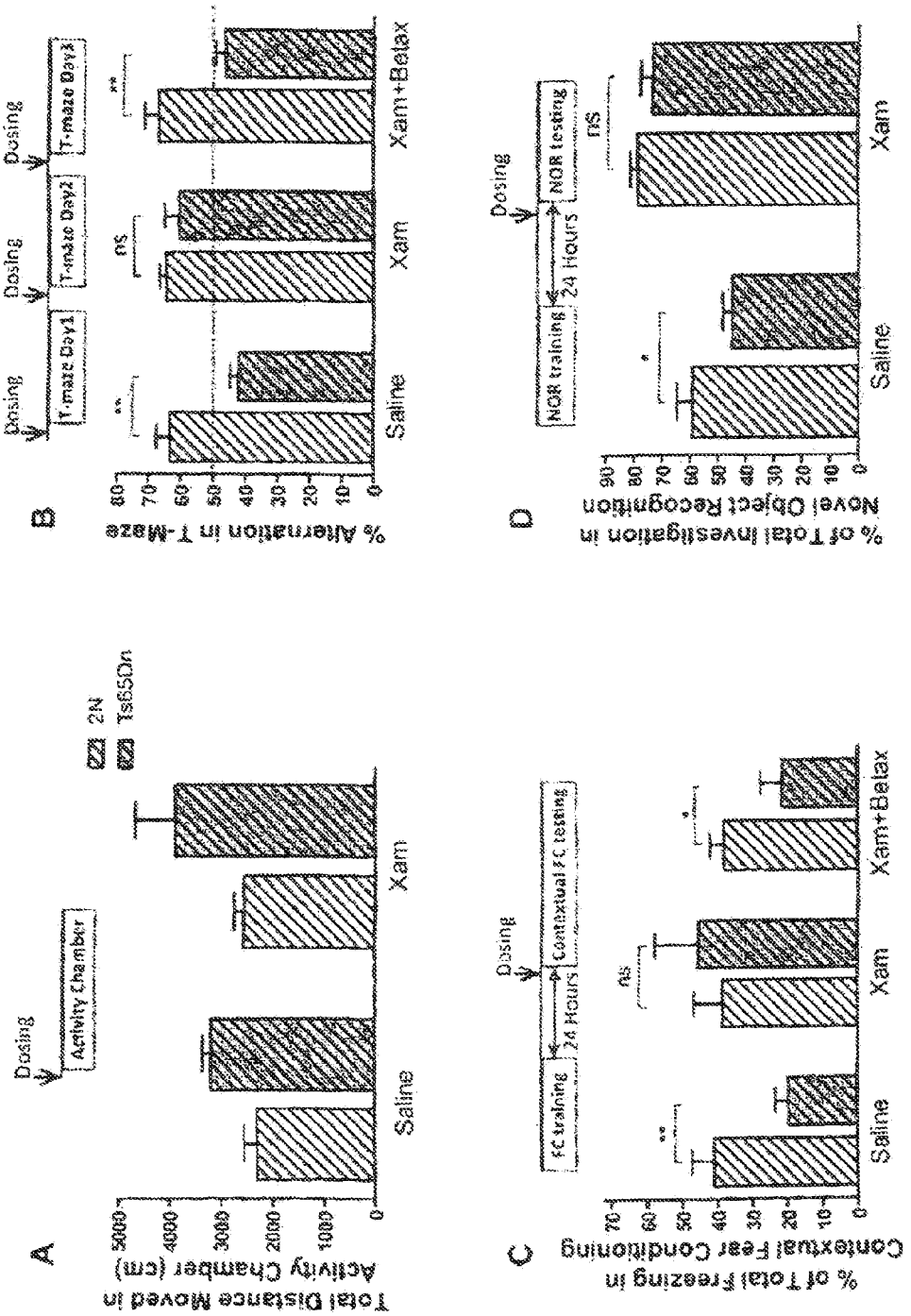

FIG. 9 Xamoterol can rescue the learning and memory in Ts65Dn mice by interaction with β1 adrenergic receptors, Shows that xamoterol can rescue learning and memory in Ts65Dn mice by interacting with $\beta_1$-adrenergic receptors (ADR). Analyzing the effect of xamoterol on total ambulatory distance moved in the Activity Chamber in male Ts65Dn mice and their control littermates (A) showed no significant effect of xamoterol in both genotypes. N(2N Saline)=9, n(Ts65Dn Saline)=7, n(2N Xamoterol)=9, and n(Ts65Dn Xamoterol)=9. Xamoterol rescued the spontaneous alternation deficit in male Ts65Dn mice, and betaxolol prevented or blocked its effect (B). n(2n Saline)=10, n(ts65Dn Saline)=7, n(2N Xamoterol)=9 and n(Ts65Dn Xamoterol)=9. Xamoterol rescued the spontaneous alternation deficit in male Ts65Dn mice, and betaxolol prevented or blocked its effect (B). n(2N Saline)=10, n(Ts65Dn Saline)=7, n(2N Xamoterol)=9, and n(the rest of experimental groups)=8. Xamoterol also rescued the memory retrieval deficit in contextual fear conditioning in male Ts65Dn, and betaxolol prevents or blocks this effect (C). n=9 for all 6 experimental groups. Xamoterol could correct the novel object recognition deficit in male Ts65Dn mice. N=8 for all 4 experimental groups. Mean+SEM is shown in all graphs. Within group comparison between Ts65Dn mice and 2N mice was analyzed, and only significant differences are shown (ns=non-significant, *–$p<0.05$, and **=$p<0.01$).

FIG. 10 Xamoterol improves the memory retrieval dose-dependently by interaction with the adrenergic receptors in central nervous system. Betaxolol impaired memory retrieval of contextual fear conditioning in C57Bl/6J mice and xamoterol reverse the impairment dose-dependently (A). Betaxolol which can cross blood-brain barrier impaired the memory retrieval in Contextual fear conditioning but atenolol which cannot get access to the brain, did not have such an effect (B). n=10 for all groups in the FC tests. In all experiments xamoterol 3 mg/kg, atenolol 3 mg/kg, and betaxolol 1 mg/kg were injected subcutaneously. Analyzing both plasma and brain samples showed that xamoterol can get access to blood and brain after subcutaneous Injection of 3 mg/kg (C and D), n=3 for each experimental groups for the plasma and brain analyzing experiment. Results are shown as mean+SEM (ns=not significant, *=p<0.05, and **=p<0.01).

DETAILED DESCRIPTION OF THE PREFERRED EMBODIMENTS

The present invention is predicated, at least in part, upon the discovery that learning and memory may be enhanced in mammals, particularly humans, that exhibit impaired learning and memory due to one or more neuro-degenerative disorders. Examples of neuro-degenerative disorders include, but are not Limited to Down Syndrome (DS) and Alzheimer's disease (AD).

More particularly, this enhancement is effected by administering at least one compound to the mammal, especially a human, which is $\beta_1$-adrenergic receptor (ADR) agonist, partial agonist or receptor ligand. Examples of $\beta_1$ adrenergic agonists include, for example, xamoterol, noradrenalin, isoprenaline, dopamine and dobutamine and the pharmaceutically-acceptable salts of any of the above. Partial agonists and ligands of the $\beta_1$-ADR are known. Further, using the methodology of Kolb et al, but for $\beta_1$-ADR instead, one skilled in the art could determine new ligands by structure-based discovery. See *Proc. Natl. Acad. Sci.* USA 2009, 106, 6843-648.

The pharmaceutically-acceptable salts may include the acid-addition salts of inorganic and organic acids, such as phosphates, sulfates, chlorides, acetates and citrates. The compound or compounds are preferably administered as salts to facilitate their administration by injection by any means, including intravenous or intramuscular injection. Suitable vehicles may include sterile water or dextrose-5%-saline, for example.

The amount administered is generally in the range of about 0.1 to 10 mg of the compound or compounds per kg of mammalian body weight. More or less may be used based on the professional discretion of the attending physician or investigator.

Exemplary mammals include mice, rats, cats, dogs, pigs and humans; however mice are preferred for experimental studies and humans are preferred for clinical treatments.

Materials and Methods

Subjects

Male and female Ts65Dn mice (B6EiC3Sn-al A-Ts $(17_{16})$ 65Dn) and their age-matched normosomic (2N) littermates, aged 9-12 months, were used in this experiment. The genotype of all animals was determined by real-time quantitative PCR before starting the experiments. Because the retinal degeneration1 mutant gene (Rd1) is carried in the background of the mice, and this gene is recessive, mice homozygous for Rd1 were not used for the study. All animals were housed in a 12 hour dark/light cycle in a temperature- and humidity-controlled environment with ad libitum access to water and food; all tests were conducted in the light cycle. All experiments were in accordance with protocols approved by the Institutional Animal Care and Use Committee of Stanford University and were performed based on the National institutes of Health Guide for the Care and Use of Laboratory Animals. All sufficient actions were considered for reducing pain or discomfort of subjects during all experiments.

Behavioral Tests

Exploratory Activity in Novel Environment

The Activity Chamber (Med associates Inc., St. Albans, Vt.) was used for the evaluation of general activity, gross locomotor activity, and exploratory behavior. Assessment took place in a square arena, 43.2×43.2 cm, with 3 planes of infrared detectors within a specially designed sound attenuating chamber, 66×55.9×55.9 cm, under dim light. The animal was placed in the center of the testing arena and allowed to move freely for 30 minutes while being tracked by an automated tracking system. Distance moved, velocity, resting time, and vertical count (rearing) were recorded.

PhenoTyper

PhenoTyper® (Noldus Information Technology, Wageningen, the Netherlands) is an automated infrared video-based observation system for the measurement of behavior of mice in their home cage {see (de Visser et al., 2006)}. The home cage environment minimizes stress or discomfort, and the subjects are given ad libitum access to all accessories in the PhenoTyper chamber. Up to 16 PhenoTypers, each containing one mouse, were connected to a computer running Ethovision XT (Noldus Information Technology, Wageningen, the Netherlands), which could acquire data over extended periods of time. After 3 days of baseline activity recording, a running wheel was placed in each cage. Distance moved, velocity of ambulatory movement and time spent in the shelter, food zone, water zone, and running wheel were measured during the experiment and reported separately for dark and light cycles.

Cat Walk

The CatWalk® apparatus (Noldus Information Technology, Wageningen, the Netherlands) consists of a glass floor illuminated with beams of fluorescent light. Assessment in a dark room allows the paws to reflect light as they come in contact with the glass floor. The bright pixel images were recorded by a camera directly below the glass walkway and digitally converted. The paw pixels were identified and analyzed by a blind observer, generating gait-related measurements (Starkey et al., 2005). Using home cage motivation, mice were trained to traverse the CatWalk apparatus 1 day prior to gait assessment. Training assures that the animals walk consistently across the walkway without hesitation or exploratory behavior. On testing day, mice were given 3 consecutive runs, returning to their home cage each time. Runs in which an animal took more than 8 seconds to cross the end zone, walked backwards, walked in the reverse direction, or reared were excluded, and the animal was allowed to run again. The average of 3 runs for each animal was reported. For this study, general gait parameters (regularity index, stride pattern, and running duration) as well as individual paw parameters (intensity, paw area, stand duration, and stride length) were analyzed.

Spontaneous Alternation

Spontaneous alternations were measured using the Y-maze and T-maze. The Y-shaped maze was constructed with 3 symmetrical white solid plastic arms at a 120 degree angle (40 cm length, 8 cm width, and 15 cm height). Each session began with placement of the mouse in the center of the maze. The mouse was allowed to freely explore the 3 arms for 8 minutes. Arm entry was defined as all 4 limbs within the arm. The maze was cleaned with 10% ethanol between sessions to eliminate odor traces. The number of arm entries and the number of triads were recorded in order to calculate the alternation percentage, which was generated by dividing the number of triads by the number of possible alternations×100. A triad was defined as a set of arm entries, when each entry was to a different arm of the maze.

The T-maze had 3 equal arms (30 cm length, 10 cm width, and 20 cm height). The start arm and 2 goal arms had guillotine gates. This test was based on the rodents' preference to experience a new arm of the T-maze instead of a familiar one (Gerlai, 1998). In each trial, the mouse was placed in the start arm. The gate was then opened and the mouse was able to freely explore the arms. As soon as the mouse entered one goal arm, the sliding gate of the other goal arm closed. The mouse eventually returned to the start arm and the next trial was started. In the next trial, the mouse may recognize the previously chosen goal arm and choose to explore a new arm rather than revisit the previously visited arm. This trial was repeated 11 times per day for 3 consecutive days, for a total of 33 trials. The maze was cleaned with 50% ethanol between trials to eliminate odor. Percent of alternation (number of turns in each goal arm) was used for analysis. This protocol has been described before by Belichenko et al. (2009) and is modified from a Deacon and Rawlins (2006) protocol (Deacon and Rawlins, 2006; Belichenko et al., 2009).

Intellicage

Home cage-based learning behaviors of socially housed mice were tested using the Intellicage® apparatus (NewBehavior AG, Zurich, Switzerland). Intellicage is an automated home cage-based system for the evaluation of place and operant learning {see (Galsworthy et al., 2005; Knapska et al., 2006) for details}. Animals were randomly assigned to Intellicages with 6-10 mice in each cage. The subjects were socially housed in these groups prior to the experiment. Fourty eight hours before introduction into the Intellicage, each animal was anesthetized by inhalation of isoflurane and injected subcutaneously with an RFID transponder (Datamars SA, Bedano, Switzerland). After general habituation to the cage, animals were subjected to the nose poke adaptation in order to learn to access the water during 2 drinking sessions every 24 hrs. Following these adaptation periods, the animals were subjected to 3 different tests: place learning, place avoidance, and entry to the novel satellite box. In the place learning test, each mouse had access to water in only one corner of the cage and learned to associate access to water with this specific corner of the cage for 4 consecutive days. In all trials, percent of correct visits during drinking sessions was reported. Following the place learning session, all animals were removed front the Intellicage. This session was followed by a 72-hr delay before all animals were returned to the Intellicage for the probe trial to evaluate the total number of visits to the correct corner. In the "place avoidance test," animals learned to avoid a corner where they were met with the aversive stimulus of an air puff. After a 4-day training session, mice were removed from the apparatus for 72 hrs and then returned to the Intellicage for a probe trial. During the probe trial, the animals received no air puffs. The percentage of visits to the previously punished corner versus all corners was reported as the percent of incorrect visits (errors) for each day. In the novelty exploration test, prior to housing of animals in the Intellicage, a smaller satellite box was attached with the entrance blocked on the end closest to the Intellicage. The mice had access to water in all corners. Then the tunnel plug was removed and the animals were allowed to freely explore the novel satellite box. The latency to the first entrance to the satellite box and visit frequency was reported.

Delayed-Matched-To-Place Water Maze

The Delayed Match-To-Place (DMP) water maze task was used to assess learning and memory as originally designed by Steel and Morris (Steele and Morris, 1999) for rats. Subjects were given a series of 4 trials approximately 8-10 min apart in a large water tank (178 cm in diameter) filled with opaque water at a temperature of 22.0±1.5° C. A 15 cm circular platform was submerged 1 cm below the water surface and placed randomly in the pool with daily changes in position. The release point in the pool was changed based on the experimental set up. Each animal was given a maximum of 90 seconds to find the submerged platform. If they were unable to find the platform in that time, the animals were physically guided to it. After remaining on the platform for 10 seconds, the animals were removed and placed in a dry cage. This process was repeated for 7 days. After training on DMP, subjects were given visible platform training to ensure they had no gross sensorimotor or visual deficit. During visible platform training, the platform was marked with a black and white ping-pong ball attached to a 10 cm wooden stick. The swim paths of the animals were recorded with the Ethovision 3.1 computer-interfaced camera tracking system (Noldus Information Technology, Wageningen, the Netherlands) and subsequently analyzed. The water was frequently changed and the tank disinfected.

Fear Conditioning and Startle Response Tests

Contextual and Cued fear conditioning was conducted for evaluation of fear-dependent learning and retrieval in the study. The test was performed using chambers from Coulbourn Instruments (Whitehall, Pa.). On the first day, the animals were placed in a chamber (Context A) for 3 min for baseline recording, followed by 5 tone-shock pairings. The shock (0.5 mA, 2 sec) was delivered following the tone (70 dB, 2 kHz, 20 sec) in each conditional/unconditional stimulus pairing. On the second day a novel chamber (Context B; new room, new olfactory environment, texture of floor, blue plastic inserts for walls, extra source of blue light, and visual cues) was used for cued testing. Three tones without shocks were presented to animals during a 3 min testing period following a 3 min pre-tone period. On the last day of the experiment, the mice were placed in Context A for 5 min without any conditional and unconditional stimulus {modified from the method described by (Saxe et al., 2006)}. Freezing was defined as the complete lack of motion for a minimum of 0.75 second as measured by FreezeFrame software (Actimetrics, Evanston, Ill.). The percent of freezing in each period was reported. For the startle response control test, an acoustic startle reflex apparatus (Med Associates Inc., St. Albans, Vt.) was used. The subjects were acclimated to the animal holder in the startle box for a total of 15 min over 3 consecutive-days prior to the experiment. The animals were exposed to 25 different trials with 10-20 second randomly variable inter-trial intervals. Five different intensities of startle pulses, 0, 90, 100, 110, and 120 dB, were randomly used, and each animal was randomly exposed 5 times to each intensity of the startle pulse. The duration of each startle pulse was 40 ms and the peak amplitude of the startle response in each trial was Three-Chambered Sociability and Social Novelty Test We Used an Established Three-Chambered Box Test (Moy et al., 2004; Crawley, 2007; Moy et al., 2007) to assess sociability and interest in social novelty. Before testing, object mice were habituated to a pencil cup 10 mm per day over 3 consecutive days. Between subjects, the box and pencil cup were cleaned with paper towels and diluted ethanol. Testing consisted of three 10-minute sessions, in the first "habituation" session, subject mice were freely allowed to investigate the three-chambered box. This was followed by a "sociability" session where a never-before-met C57Bl/6J male mouse was placed in one of the pencil cups. The location of the stranger mouse was alternated from left to right across subject testing. In the "social novelty" session, a second never-before-met C57Bl/6J male mouse was placed under the second pencil cup. Trials were video recorded for subsequent rating. Measured parameters were number of entrances into the chambers, time spent in chambers, and time spent sniffing the pencil cups.

Social Memory Testing

Prior to social memory testing, randomly selected individually housed ovariectomized C57Bl/6J female mice (OEF) were put into the home cages of subject mice 4 hrs per day for 5-7 days to reduce sexual behavior.

Two-Trial Jest:
A never-before-met OEF was placed into the home cage of a test animal for 5 rain and then removed. After an inter-trial interval (ITI) of 30 mm, the same OEF was placed back in the home cage together with a novel never-before-met OEF for 5 mm. Trials were videotaped and analyzed as in the five-trial social memory test.

Five-Trial Test:
A single OEF was introduced into the home cage of a never-before-met test animal for four 1-min exposures with an inter-trial interval of 10 min. In a fifth trial 10 min later, instead of the familiar OEF, a novel, never-before-met OEF was put into the home cage of the test animal for 1 min. All trials were videotaped and subsequently analyzed for olfactory investigation. Investigation was defined as nose-to-body contact of the test animal versus the intruder. Total investigation, including ano-genital investigation, perioral investigation, and body investigation were measured in two 30-second bins.

Olfactory Habituation Test

The test consisted of 2-min presentations of 6 different cotton swabs soaked with 100 μL of liquid separated by 3-min ITI's. The tip of the cotton swab was placed 1 cm above the bedding in the home cage to allow investigation without rearing. After 3 presentations of distilled water, the animals received 3 presentations of either pure urine from a never-before-met singly housed OEF mouse or almond scent (1:100 in distilled water). Trials were videotaped for subsequent scoring. Direct physical contact between the nose and the cotton swab was scored; chewing the cotton swab was excluded.

Pharmacological Experiment

For testing the role of $\beta_1$ adrenergic receptors ($\beta_1$-ADR) in cognitive deficits of Ts65Dn mice, xamoterol, a selective $\beta_1$ partial agonist, and betaxolol, a selective $\beta_1$ antagonist, were used. In this part of the study, activity chamber and three cognitive tests, including T-maze spontaneous alternation, contextual fear conditioning (CFC), and novel object recognition were performed. In T-maze spontaneous alternation and contextual fear conditioning, both Ts65Dn and 2N male mice were divided into three treatment groups including normal saline (Vehicle), xamoterol, and betaxolol plus xamoterol groups. In the novel object recognition test, both Ts65Dn and 2N male mice were divided into two treatment groups, normal saline and xamoterol. The T-maze was performed exactly as previously described. Since Ts65Dn mice showed a significant deficit in contextual fear conditioning, the tone cued testing paradigm was deleted from the fear conditioning protocol in this part of the study. On the first day (training day), animals were placed in the fear conditioning chamber, and after a 3-minute pre-shock period, they were exposed to 5 shocks (2 s, 0.5 mA,) with inter-trial intervals of 80 seconds and no tone. On the second day, the animals first received xamoterol, xamoterol plus betaxolol, or saline injection, and one hour later, they were placed in the same chamber for 5 minutes. Similar to the previous description of fear conditioning, freezing was defined as the complete lack of motion for a minimum of o.75 second. The Novel Object Recognition task is conducted in an open field arena (40 cm×40 cm). Mice were habituated in the testing room for 1 hour followed by 5 minutes habituation inside the arena without any objects. On 4th day animals were introduced 3 times to arena with 3 identical subjects for 10 minutes with 3 minutes inter trial intervals. On 5th day (24 hours after trainings) one of the objects replaced by a novel one and the time sniffing of each object were used for analysis.

Drugs

For testing the role of $\beta_1$ adrenergic system, xamoterol and betaxolol (Tocris Bioscience, Ellisville, Mo.) were injected subcutaneously using 10 ml/kg normal saline as vehicle. Xamoterol, (3 mg/kg) was given one hour before testing and betaxolol (1 mg/kg) was given 30 minutes before testing.

Statistical Analysis

All data were presented as Mean±/+SEM, and $p<0.5$ was considered statistically significant. Two-way ANOVA was used for the evaluation of the effect of genotype and sex in the activity chamber, CatWalk, T-maze, Y-maze, 3-chambered sociability and social novelty, and 2-trial social memory tests. Repeated measure two-way ANOVA was used for analyzing the training period of place learning and place avoidance, and also the number of satellite box visits in the novelty exploration test in the Intellicage experiment. Repeated measure ANOVA was also used for evaluation of the escape latency in DMP, fear-conditioning, startle response, 5-trial social memory, and olfactory control tests. ANOVA also used for analyzing the pharmacological experiment. The Bonferroni posthoc test was used when appropriate. For analyzing PhenoTyper data, three-way ANOVA was used for the main effects of genotype, sex, and light cycle. The Student t-test was used as a post test when appropriate. The Student t-test was also used for comparing Ts65Dn mice and 2N controls in probe trials and for the comparison of latency of the first visit to the satellite box in the Intellicage. Novelty exploration, time savings in DMP, and percent of freezing in fear conditioning was also examined using Student t-test. In the spontaneous alternation experiments, one sample t-test was used for comparison of alternation to chance level (50%).

Results

Three groups of behavioral tests were conducted in this comprehensive set of behavioral phenotyping assays (see Table 1 below). Structure(s) involved for each behavioral test have been summarized based on our current knowledge in Table 1. A condensed summary of behavioral outcomes in this study is also shown in Table 2 below.

Exploratory Activity in Novel Environment

Figure 1:
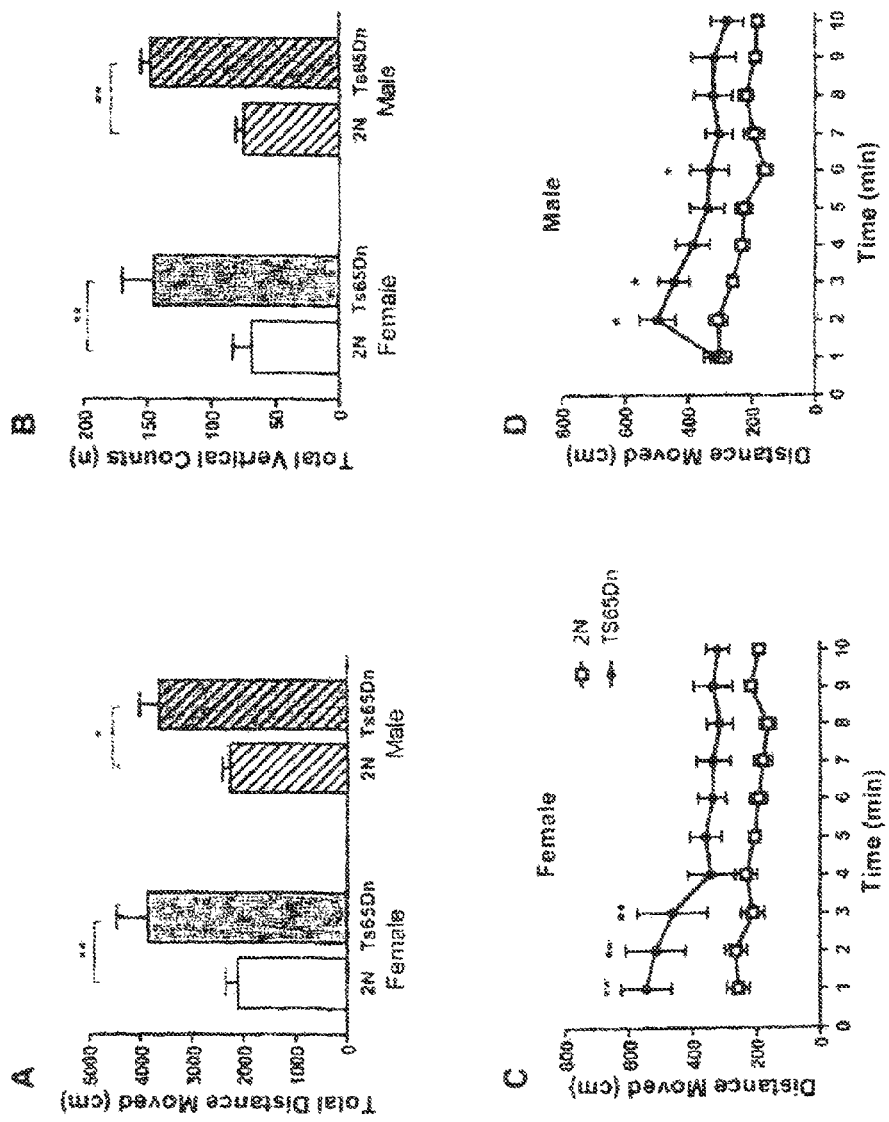
FIG. 1 Exploratory activity in a novel environment in male and female Ts65Dn and 2N mice illustrates short term novel environment exploratory activity. Ambulatory distance moved (A, C and D) and total vertical count (B) in the Activity Chamber in male and female Ts65Dn mice and their control littermates are presented. Mean/SEM is shown, n=10 in all groups. Total ambulatory distance moved and total vertical count in Ts65Dn mice were both significantly higher than 2N mice was analyzed and only significant differences are shown. (*=p<0.05 and **=p<0.01).

Exploratory behavior in a novel environment and general locomotor activity were assessed in automated activity chambers. As compared to 2N controls, both male and female Ts65Dn mice showed increased distance traveled during a 10 min testing period in the novel environment (FIG. 1A; effect of genotype, $F_{1, 36}=6.93$, p=0.0002; effect of sex, $F_{1, 36}=0.009$, p=0.925; effect of genotype in female, p<0.01 and in male, p<0.05). Indeed, the distance moved by Ts65Dn mice was nearly twice that of 2N mice. In addition, when minute to minute movement of animals in the novel box was studied, higher locomotor activity was observed in both male and females (FIGS. 1C and D; effect of genotype for females, $F_{1, 162}=7.59$, p=0.013; effect of genotype for males, $F_1$, rearing in the novel environment compared to 2N mice (FIG. 1B; effect of genotype, $F_{1, 36}=22.30$, p=0.000; effect of sex, $F_{1, 36}=0.531$, p=0.47; effect of genotype both in female and male, p<0.01). The velocity of ambulatory movement in Ts65Dn mice was not significantly different from control littermates. Consistent with this finding was that Ts65Dn mice had a significantly shorter resting time than control mice.

PhenoTyper

Figure 2:
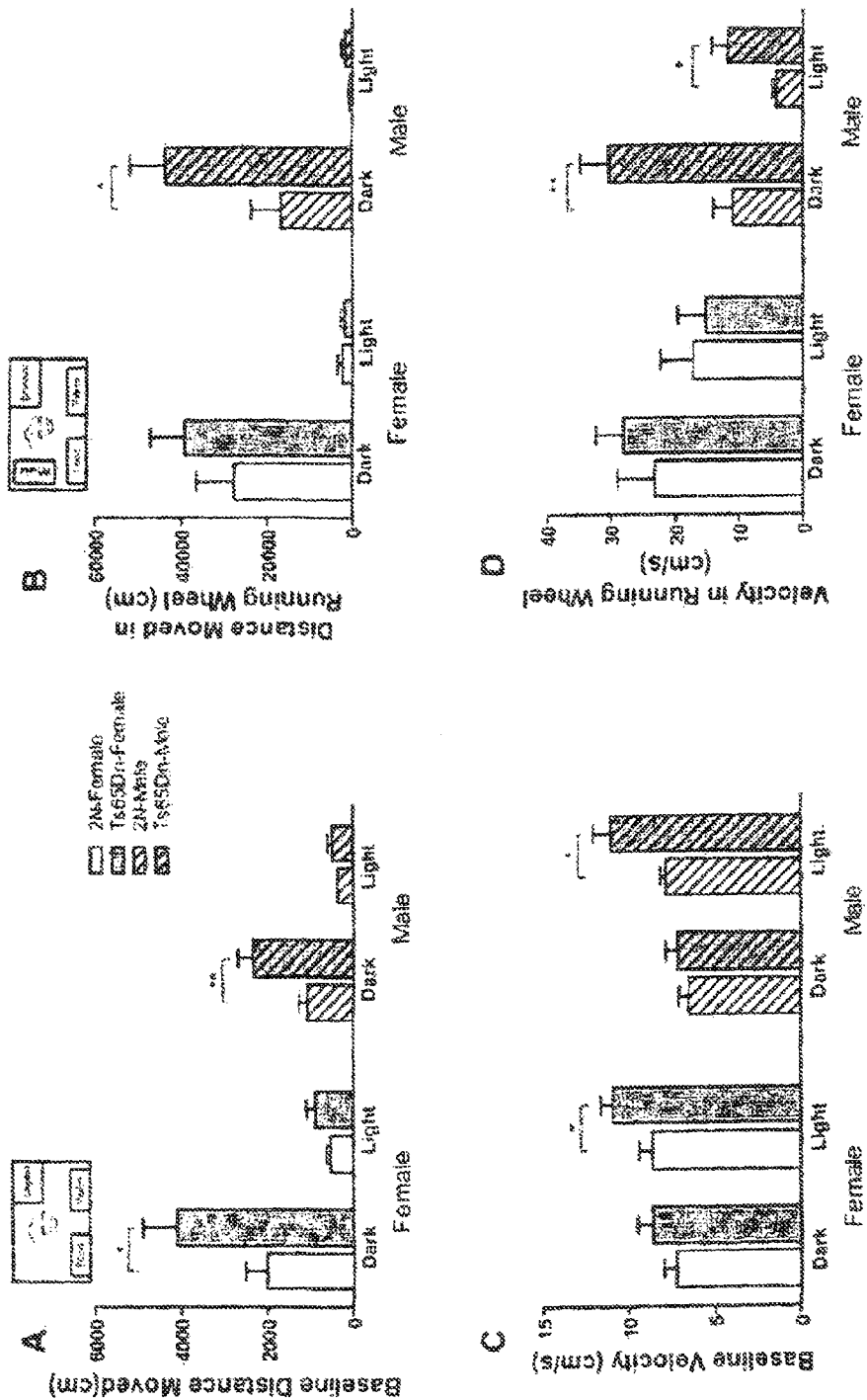
FIG. 2 Automated home cage activity monitoring in male and female Ts65Dn and 2N mice activity parameters of male and female Ts65Dn mice and 2N controls during dark and light cycle in PhenoTyper including baseline distance moved in each hour (A), distance moved in each hour after introducing running wheel (B), baseline velocity of movement (C), velocity in running wheel (D), time in shelter during baseline (E), and alter introducing running wheel (F) are presented. Both distance moved and velocity, during baseline and after introducing the running wheel, were higher in Ts65Dn mice than 2N mice (main effect of genotype). Ts65Dn mice spent less time in the shelter than 2N mice during baseline and also after introducing the running wheel. Mean+ SEM is shown and n=8 for all groups. Within group comparison between each pair of genotypes was analyzed and only the significant differences are shown (*=p<0.05 and **=p<0.01).

In order to study further locomotor activity of Ts65Dn mice, and to do so in a stress-free environment, animals were monitored continuously in the home cage during both light and dark cycles using the PhenoTyper. Recordings were conducted for 3 days at baseline and for 3 days following introduction of a running wheel. As in the novel environment, Ts65Dn mice were observed to move a greater distance than 2N controls during baseline monitoring. The distance moved during the dark cycle was significantly greater than that in the light cycle, and female subjects moved more than males (FIG. 2A; effect of genotype, $F_{1, 64}=13.66$, p=0.001; effect of sex, $F_{1, 64}=9.70$, p=0.003; effect of cycle, $F_{1, 64}=48.05$, p<0.0001). The differences observed during the light cycle were not significant (p>0.05 for both males and females). Therefore, Ts65Dn mice are more active than 2N mice in dark cycle but not in light cycle. Introduction of the running wheel promoted a marked ~10-fold increase in locomotor activity in both Ts65Dn and 2N mice. As compared to 2N controls, the activity of Ts65Dn mice was significantly greater (FIG. 2B; effect of genotype, $F_{1, 62}=6.04$, p=0.017; effect of cycle, $F_{1, 62}=57.76$, p<0.0001; effect of sex, $F_{1, 62}=0.27$, p=0.604). As for baseline recordings, activity differences during the light cycle did not discriminate Ts65Dn mice and controls. The velocity of movement during baseline recordings showed that Ts65Dn mice moved faster than 2N mice during the light cycle, and that the velocity during light cycle was greater than the dark cycle (FIG. 2C; effect of genotype, $F_{1, 64}=13.05$, p=0.001; effect of cycle, $F_{1, 64}=17.93$, p<0.001; effect of sex, $F_{1, 64}=1.90$, p=0.173). With the addition of the running wheel, the velocity of movement for male Ts65Dn mice was significantly higher than 2N mice during both the dark and light cycles (FIG. 2D; effect of genotype, $F_{1, 60}=6.74$, p=0.012; effect of sex, $F_{1, 60}=5.26$, p=0.026; effect of cycle, $F_{1, 60}=14.57$, p<0.0001). Both 2N and Ts65Dn mice spent more time in the running wheel during the dark than light cycle. However, only male Ts65Dn mice spent significantly more time in the running wheel during dark cycle compared to 2N mice Ts65Dn mice spent less time in the shelter than 2N mice during dark cycle. For both genotypes, time spent in the shelter during the dark cycle was less than the light cycle, but there was no significant effect of sex on shelter time (FIG. 2E; effect of genotype, $F_{1, 56}=16.76$, p<0.0001; effect of cycle, $F_{1, 56}=41.29$, p<0.0001; effect of sex, $F_{1, 56}=1.01$, p=0.319). Introduction of the running wheel to the cage resulted in reduced time spent in the shelter in Ts65Dn as compared to 2N mice. Shelter time during the dark cycle was less than the light cycle, but female and male mice showed different patterns in time spent in the shelter in the light cycle after introducing the running wheel (FIG. 2F; effect of genotype, $F_{1, 64}=16.74$, p<0.0001; effect of cycle, $F_{1, 64}=60.26$, p<0.0001; effect of sex, $F_{1, 64}=17.09$, p<0.0001). During the dark cycle, Ts65Dn mice spent more time in the water and food zones than 2N mice during both the baseline period and after addition of the running wheel. However, during the light cycle Ts65Dn mice spent more time than 2N mice in food zone but not the water zone.

CatWalk

Figure 3:
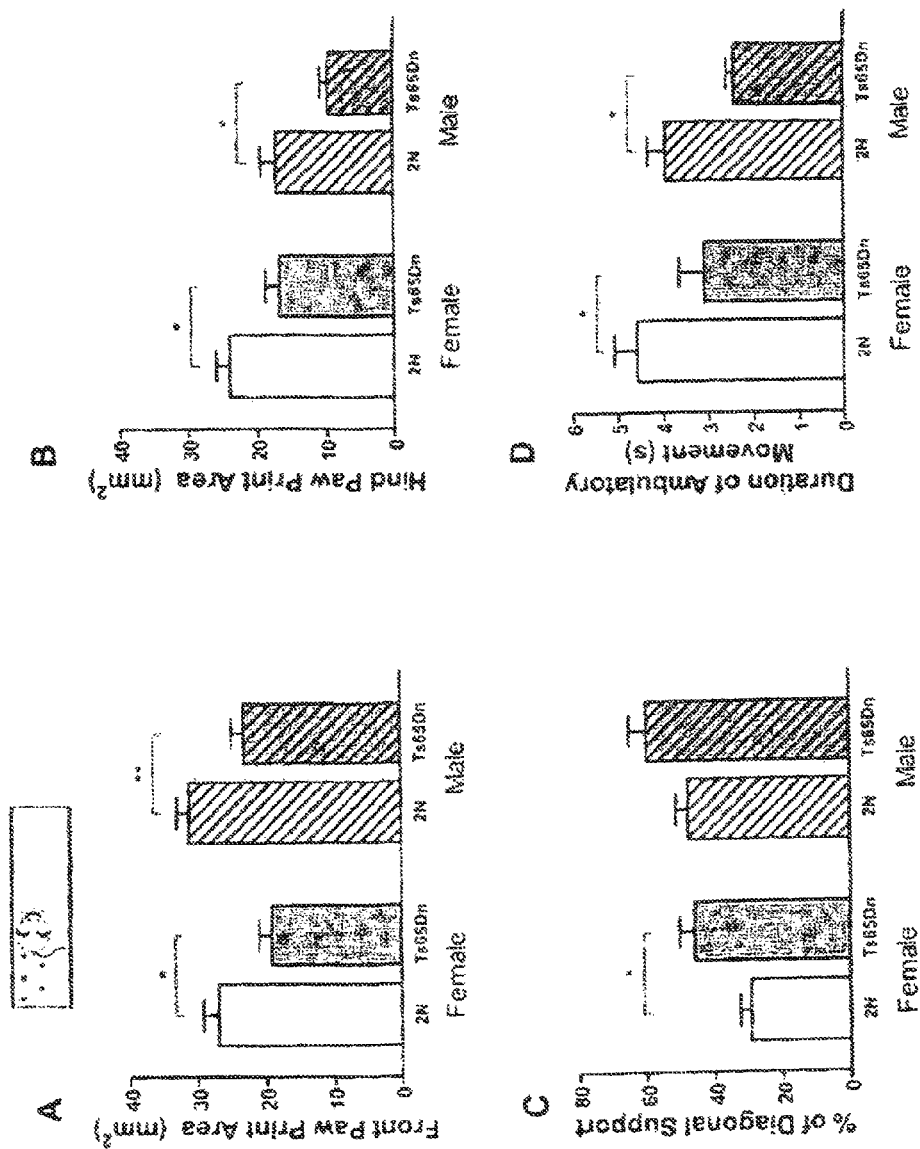
FIG. 3 Automated gait analysis by CatWalk in male and female Ts65Dn and 2N mice illustrates an automated gate analysis by CatWalk. Front paw print area (B), percent of diagonal support (C), stand duration for front paw (D) and hind paw (E), and total duration of ambulatory movement on walkway (F) are presented. Ts65 Dn mice showed significantly smaller paw print area, a higher percentage of diagonal support, shorter stand duration, and shorter duration of ambulatory movement compared to 2N controls (main effect of genotype). In all graphs Mean+SEM of parameters are shown and n (male and female 2N)=10 and n(male and female Ts65Dn)=11. Within group comparison between Ts65Dn and 2N mice was analyzed and only the significant differences are shown (*=$p<0.05$ and **=$p<0.01$).
Figure 4:
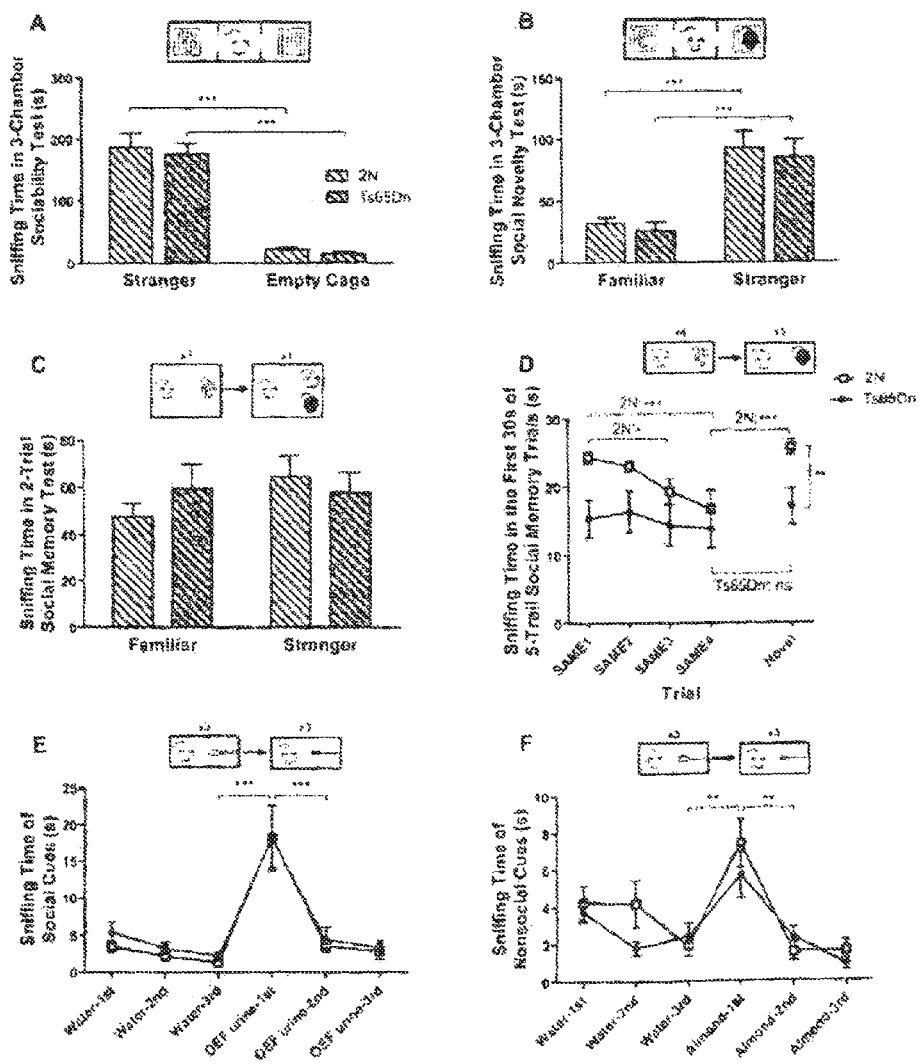
FIG. 4 Sociability, social novelty and social memory in 2N and Ts65Dn mice.

In order to further study differences in locomotor activity, CatWalk, a quantitative gait analysis system for evaluating coordination and gait were used. While the activity chamber and the PhenoTyper can assess gross locomotor deficit, the CatWalk can show detailed impairment of each individual paw. Both female and male Ts65Dn mice had significantly smaller paw print areas compared to 2N mice, both in the front paw (FIG. 3A; effect of genotype, $F_{1, 38}=17.48$, p=0.0002; effect of sex. $F_{1, 38}=4.417$, p=0.042) and hind paw (FIG. 3B; effect of genotype, $F_{1, 38}=16.45$, p=0.0002; effect of sex, $F_{1, 38}=14.49$, p=0.0005). Statistical analysis showed that the front paw print area in males was larger than females, and conversely, the hind paw print area in males was smaller. Intensity of both the front and hind paw print in Ts65Dn mice was lower than 2N mice, and in males the intensity was lower than in females. Since body weight of animals can affect the paw print area, the body weight of Ts65Dn and 2N mice were analyzed. The weight of male Ts65Dn mice was lower than 2N mice (38.23±1.37 and 46.52±2.09 grams respectively; p=0.004) but there was no difference between the body weight of the female Ts65Dn and 2N mice (34.55±2.43 and 34.2±2.16 grams respectively, p=0.917). Furthermore, a significant difference was detected in the diagonal support of the Ts65Dn mice, which measures the percentage of time an animal's right forepaw and left hind paw, or left forepaw and right hind paw, are simultaneously in contact with the floor during strides. Ts65Dn mice showed higher diagonal support than 2N mice and male mice showed a higher percentage of diagonal support compared to females (FIG. 3C; effect of genotype, $F_{1, 38}=11.72$, p=0.0015; effect of sex, $F_{1, 38}=14.95$, p=0.0004). Higher diagonal support indicates that Ts65Dn mice spend more time in ambulatory motion. The regularity index was another reported parameter. Regularity index expresses the number of normal step sequence patterns relative to the total number of paw placements. There was no significant difference in regularity index between Ts65Dn and 2N mice or between male and female mice. Rodents use 6 possible step sequence patterns during walking. Among these patterns, the Ab pattern is the most frequent. In this pattern, the animals use in sequence their left front paw, right hind paw, right front paw, and left hind paw. To analyze the step pattern, an inter-limb coordination parameter, the percent incidence of the Ab pattern between Ts65Dn and 2N mice during trials was analyzed; no significant difference was seen. There was no significant difference between Ts65Dn and 2N mice in the front and hind paw base of support, which is the distance between the center of the right and left paw. Therefore, these animals do not have a deficit in balance. There was no significant difference in stride length of the front paw or hind paw between male and female mice, and there was no effect of genotype on the stride length of the front paw, but stride length of the hind paw was longer in Ts65Dn than 2N mice. Ts65Dn mice showed differences in stand duration in both front and hind paws. Stand duration of the front paw in Ts65Dn mice was less than 2N controls and less in male than female mice (FIG. 3D; effect of genotype, $F_{1,\ 38}=17.48$, p=0.0002; effect of sex, $F_{1,\ 38}=4.42$, p=0.042). Similar findings were seen in hind paw stand duration (effect of genotype, $F_{1,\ 38}=16.45$, p=0.0002; effect of sex, $F_{1,\ 38}=14.49$, p=0.0005). Swing speed was not significantly different in Ts65Dn mice compared to 2N controls, both in the front, paw and hind paw, but the swing speeds were lower in male than female mice. Total duration of ambulatory movement shows the time it takes for the mouse to move from the start to the finish zone. Total duration for the Ts65Dn was shorter compared to 2N mice (effect of genotype, $F_{1,\ 38}=12.21$, p=0.001; effect of sex. $F_{1,\ 38}=2.29$, p=0.138) indicating that Ts65Dn mice were walking across the walkway in a shorter time than the 2N mice.

Spontaneous Alternation

The T-maze and Y-maze were used for assessment of spontaneous alternations for spatial working memory. The mouse learns to alternate between two arms of T-maze or three arms of Y-maze to have a chance to explore a new arm and avoid revisiting the previous one(s). Ts65Dn mice showed a significantly smaller rate of continuous spontaneous alternation than 2N controls in the Y-maze; there was no significant effect of sex on alternation rate (FIG. 5A; effect of genotype, $F_{1,\ 27}=6.95$, p=0.014; effect of sex, $F_{1,\ 27}=3.94$, p=0.057). Comparing alternation rate with chance level (50%), a one sample t-test showed that female 2N and Ts65Dn mice and male 2N mice alternated significantly more than chance level (p<0.01). However, the alternation rate in male Ts65Dn mice was not significantly different from the chance level (p>0.05), which indicates deficit in spontaneous alternation. The number of entries to the arms of the Y-maze was significantly higher in Ts65Dn than 2N mice (FIG. 5B; effect of genotype, $F_{1,\ 27}=12.10$, p=0.002; effect of sex, $F_{1,\ 27}=0.50$, p=0.485). Increased number of entries to the arms of the maze signifies the hyperactivity of Ts65Dn mice.

Similar to the Y-maze, the alternation rate of Ts65Dn mice was significantly lower than 2N mice in the T-maze, and there was no significant difference between female and male animals (FIG. 5C; effect of genotype, $F_{1,\ 28}=33.88$, p<0.0001; effect of sex, $F_{1,\ 28}=0.07$, p=0.796). Both female and male 2N control mice alternated significantly more than chance level (p=0.002, female, and p=0.0004, male in one sample t-test compared to 50%). Spontaneous alternation in Ts65Dn mice was not statistically different from the chance level (p=0.702 for female and p=0.230 for male).

Intellicage

Intellicage, a novel automated system, was used to investigate place preference and place avoidance learning as well as exploratory behavior of Ts65Dn mice in the home cage environment. Female Ts65Dn mice did not show a significant deficit in acquisition of place learning (effect of genotype, $F_{1,\ 45}=0.74$, p=0.403; effect of training day, $F_{3,\ 45}=11.82$, p=0.0005). Also, they showed no significant difference in the probe trial at 72 hrs (p=0.21). In the avoidance learning test, Ts65Dn (nice visited the punished corner similarly to 2N mice during training days (effect of genotype, $F_{1,\ 39}=2.36$, p=0.149; effect of training day, $F_{3,\ 39}=27.12$, p<0.0001). However, Ts65Dn showed a significant deficit in the probe trial of the previously punished corner after 72 hrs (p=0.042) in place avoidance learning. In the novelty exploration test, after opening the connection between the main compartment of the cage and the novel satellite box, the Ts65Dn mice showed a significant reduction in the number of visits to the novel box, as compared to 2N controls (effect of genotype, $F_{1,\ 42}=5.13$, p=0.04 and for effect of time, $F_{3,\ 42}=8.22$, p=0.0001). However, the latency for the first entry to satellite box was significantly shorter for the Ts65Dn mice than for 2N mice (FIG. 5F; p=0.027).

Delayed-Matched-to-Place Water Maze

In the visible platform experiment both female and male Ts65Dn mice showed no significant difference in swimming velocity compared to 2N controls. All female and male Ts65Dn and 2N mice found the visible platform, except for one female animal which was unable to find the visible platform during all 4 trials of the task; therefore, it was excluded from the study.

The DMP water maze tests spatial working/episodic-like memory. Both female and male Ts65Dn mice showed significant differences in escape latency compared to controls indicating a deficit in the spatial reference memory (FIGS. 7A and 8; effect of genotype, in female, $F_{1,\ 42}=10.61$, p=0.006 and in male, $F_{1,\ 42}=24.98$, p=0.0002; effect of trial number, in female, $F_{3,\ 42}=3.59$, p=0.021 and in male, $F_{3,\ 42}=7.82$, p=0.0003).

Fear Conditioning and Startle Response Test

The Startle response test was run to evaluate the ability of subjects to respond to tone cues in fear conditioning. Neither female nor male Ts65Dn mice showed a significant deficit in the startle response test (FIGS. 8E and F; effect of genotype in female, $F_{1,\ 56}=0.17$, p=0.682; effect of genotype in male. $F_{1,\ 56}=1.13$, p=0.306). Tone-cued and contextual fear conditioning was tested for evaluation of Pavlovian learning and memory. FIGS. 8A and B show the overall learning in fear conditioning test during training day in different inter-trial intervals (ITIs) for both males and females. There was no significant difference in training day ITIs between Ts65Dn and 2N mice in both females (effect of genotype, $F_{1,\ 90}=0.03$, p=0.861) and males (effect of genotype, $F_{1,\ 180}=0.29$, p=0.59). In tone-cued fear conditioning in a novel context, the Ts65Dn mice exhibited less freezing than 2N mice. However, this difference was not statistically significant (FIGS. 8C and D; p=0.517 for females and p=0.071 for males). In day 3 of the contextual retention test, both male and female Ts65Dn mice showed significantly less freezing (p=0.049 for females and p=0.038 for males) than their 2N littermates. These results indicate that Ts65Dn mice have a deficit, in memory retrieval in contextual fear conditioning.

Social Interaction Tests

Sociability and interest in social novelty was assessed using a three-chambered test. In the 10 minute "habituation"

session, Ts65Dn and 2N mice did not exhibit a side preference for the left or the right chambers. During the subsequent 10 minute "sociability" session, both Ts65Dn and 2N controls preferred to sniff at a cage containing a stranger mouse than sniffing at an empty cage as a non-social object (effect of genotype, $F_{1, 18}$=0.34, p=0.567; effect of object, $F_{1, 18}$=97.71, p<0.0001). Both genotypes also spent significantly more time in the chamber with the stranger mouse versus the chamber with the empty cage. In the first 5 minutes of the "social novelty" session, Ts65Dn and 2N mice spent significantly more time sniffing the novel stranger than the now familiar social object (effect of genotype, $F_{1, 18}$=0.26, p=0.616; effect of novelty of the social object, $F_{1, 18}$=59.17, p<0.0001). Both genotypes preferred the chamber containing the stranger over the chamber containing the familiar mouse. Social memory abilities were measured in 2 different tests: the two-trial social memory test and five-trial social memory test. In the two-trial test, Ts65Dn did not exhibit a preference for the novel versus the familiar intruder, whereas 2N mice showed a trend for such a preference which was not statistically significant (effect of genotype, $F_{1, 15}$=0.053, p=0.821; effect of object mouse, $F_{1, 15}$=2.487, p=0.281). In the five-trial social memory test, animals were subjected to 4 repeated pairings with the same OEF followed by a pairing with a novel OEF. Analysis of the first 30-second bins revealed a significantly different result in Ts65Dn and 2N mice (effect of genotype, $F_{1, 68}$=4.936, p=0.040; effect of trial, $F_{4, 68}$=6.634, p<0.0001). 2N mice exhibited a significant habituation response to repeated exposures to the familiar OEF and a dishabituation response to a novel OEF (first vs. third trial p<0.05; first vs. fourth trial p<0.0001; fourth vs. fifth trial p<0.0001). In contrast, Ts65Dn mice showed a persistent level of interest in both the familiar and novel stimulus OEF (p>0.05). Analysis of the final 30 seconds revealed a significant habituation response for both genotypes, a significant dishabituation for 2N, and non significant dishabituation trend for Ts65Dn mice. Since recognition of individuality is thought to be transmitted by olfactory cues, we measured responses to non-social and social olfactory cues. Ts65Dn mice were comparable to 2N mice in showing both a significant habituation response to social (effect of genotype, $F_{1, 90}$=0.24, p=0.633) as well as to non-social olfactory cues (effect of genotype, $F_{1, 90}$=0.97, p=0.337).

Pharmacological Experiments

We have recently shown that restoration of norepinephrine level using L-threo-3,4-dihydroxyphenylserine (L-DOPS) in Ts65Dn mice restored the hippocampal-mediated contextual deficit in fear conditioning and nesting behavior (Salehi et al., 2009). In order to study the role of $\beta_1$-ADR in mediation of these behavioral effects, we used the selective $\beta_1$ receptor agonist xamoterol and the $\beta_1$ receptor antagonist betaxolol in our current studies. To control for general effect of novel compound dosed, the locomotor activity was monitored post dosing. Xamoterol did not show a significant effect on locomotor activity of male Ts65Dn (FIG. 9A; effect of treatment, $F_{1, 30}$=1.148, p=0.293; effect of genotype, $F_{1, 30}$=6.168, p=0.019. However, xamoterol rescued the deficit observed in T-maze spontaneous alternation, and its effect was blocked by the $\beta_1$-ADR antagonist, betaxolol (FIG. 9B; the effect of treatment, $F_{2, 44}$=3.879, p=0.0281; the effect of genotype, $F_{1, 44}$=27.38, p<0.0001). Xamoterol also improved the memory retrieval of Ts65Dn mice in contextual fear conditioning similar to T-maze test, and the effect of xamoterol was completely blocked by betaxolol (FIG. 9C). Vehicle treated Ts65Dn group showed a significant deficit in contextual fear conditioning (p<0.01) compared to the 2N control group while no significant differences between 2N control and xamoterol treated group observed (p=0.648). Simultaneous treatment with both betaxolol and xamoterol prevented the effect of xamoterol, and there was a significant difference in percent of freezing between 2N and Ts65Dn mice in this group (p<0.05). In novel object recognition, xamoterol corrected the novel object recognition deficit in Ts65Dn mice and had no effect on 2N mice performance (FIG. 9D, the effect of genotype, $F_{1, 28}$=5.53, p=0.026; the effect of treatment $F_{1, 28}$=35.05, p<0.0001)

Discussion

The Ts65Dn mouse model of DS with a segmental trisomy of Chromosome 16 was introduced by Davisson et al. (Davisson et al., 1990; Davisson et al., 1993). For over two decades, this preclinical model has frequently been used in behavioral phenotyping and pharmacological screening studies. In this study, we aimed to conduct a comprehensive phenotyping of these mice in order to identify robust and reproducible behavioral abnormalities in sensorimotor, exploratory, learning, memory, and social paradigms. Our effort identified the hippocampal-mediated learning and memory tasks to be a severely affected phenotype in these animals. Since we had recently demonstrated that the norepinephrine (NE)-ergic projection to hippocampus plays an important role in retrieval of contextual memory in these animals (Salehi et al., 2009), we explored the role of the $\beta_1$-ADR as therapeutic target for treatment of learning and memory deficits in this model of Down Syndrome.

Locomotion in Ts65Dn Mice

It has been reported that children between ages of 6 and 11 years with DS are hyperactive compared to their typical peers (Pueschel et al.; 1991). The Ts65Dn mice also displayed a higher overall locomotor activity, both in the home cage and a novel testing environment. The prefrontal cortex and hippocampus play important roles in the behavior of animals, is shown by observed hyperactivity after prefrontal or hippocampal lesion in rodents (Kolb, 1974; Tani et al., 2001; Katsuta et al., 2003; Viggiano, 2008). Pathological and chemical abnormalities in hippocampus observed in Ts65Dn mice (Belichenko et al., 2004) or altered cholinergic neurotransmission (Granholm et al., 2000; Seo and Isacson, 2005) may be responsible for this observed hyperactivity in Ts65Dn mice. These results are in line with reports describing the hyperactivity of male and female Ts65Dn mice in open field and activity chambers (Davisson et al., 1993; Reeves et al., 1995; Coussons-Read and Crnic, 1996). Stewart et al. (2007) showed that Ts65Dn mice between the ages of 4-6 months were more active than their control littermates in the light cycle, while their activity in the dark cycle was not significantly different from 2N (Stewart et al., 2007). In contrast, our results indicate a significantly higher home cage activity in trisomic mice compared to the 2N controls in the dark cycle, but not during the light cycle. These discrepancies could be due to differences in the age of animals tested or experimental conditions. In our study, the activity of animals was monitored using an infrared video recording system remotely, continuously, and without any disturbance, in as opposed to previous studies taking snapshot of the animals' behavior in a novel context. In line with previous publications reporting the jumping and repetitive behavior of Ts65Dn animals (Reeves et al., 1995; Turner et al., 2001), we also found increased rearing and jumping behavior in both male and female Ts65Dn mice. Isolation of mice during testing in the activity chamber might be triggering this behavior and may indicate that isolation and single housing of Ts65Dn mice is an anxiety-inducing factor leading to repetitive jumping behavior. When the running wheel was introduced to the home cage as a novel stimulus, male Ts65Dn mice showed longer wheel activity compared to the 2N mice, a difference which was not observed in female Ts65Dn mice. This increased activity on the running wheel agrees with the repetitive behavior observed in isolation as previously described (Stewart et al., 2007).

It has been shown that children with DS suffer from balance and postural deficits and gait pattern abnormalities (Shumway-Cook and Woollacott, 1985; Galli et al., 2008). DS children also adopt a more flexed posture of the hip and knee joints and increased fluctuation of ankle movement during the walking cycle (Parker et al. 1986). However, there are controversial reports related to motor function of Ts65Dn mice. Costa et al. (1999) showed that Ts65Dn mice have a deficit in motor coordination in the rotarod test (Costa et al., 1999) (Baxter et al., 2000; Hyde et al., 2001b). In order to investigate this further in the Ts65Dn mice, we used the CatWalk automatic gait analysis software and hardware. Ts65Dn mice had a smaller paw print area and also applied lower pressure on their paws, which manifests as faster strides on the walkway and can be interpreted as toewalking. Hampton et al. (2004) also reported a faster walking speed, shorter stride length, and significant difference in gait dynamics in 10-12 week-old male Ts65Dn mice using a motorized treadmill (Hampton et al., 2004). In our study we found no significant difference in step pattern or regularity index which expresses the number of normal step sequences relative to the total number of paw placements using this automated system. In summary, our results indicate that Ts65Dn mice show increased locomotor activity in the home cage as well the novel environment. The hyperactivity observed does not seem to be driven by the novelty of testing environment. This looks like a general non-selective increased activity which also observed in the home cage and could be due to decreased inhibition.

Learning and Memory in Ts65Dn Mice

DS in children is associated with severe impairment in hippocampal-dependent tasks (Pennington et al., 2003) and spatial learning (Wishart et al., 1993; Nadel, 2003), along with significant deficits in cognitive and language development (Abbeduto et al., 2007). In order to investigate learning and memory deficits in the segmental trisomic mouse model of Down Syndrome, Ts65Dn mice were tested in both standard and novel learning and memory tests. To further evaluate learning and memory in Ts65Dn mice under social housing in the home cage environment, female mice were also tested in Intellicage and automated home cage testing (Galsworthy et al., 2005). Both Ts65Dn and 2N mice demonstrated identical place learning during task acquisition as well as retrieval which may indicate that these mice could have normal learning in a stress-free and simple environment. However, introduction of air puffs as an aversive stimulus in an avoidance protocol revealed a significant behavioral deficit in Ts65Dn. Ts65Dn mice showed no deficit in acquisition of the task. They learned to avoid the punished corner similar to 2N mice, but showed significant deficit in memory retrieval after 72 hrs. Our results suggest that the Ts65Dn mice do not exhibit learning and memory deficits in a stress-free home cage environment, as was indicated by the place learning protocol used here. However, introduction of a stressful stimulus such as an air puff revealed the avoidance deficit in these mice. This may indicate that stress during standard behavior tests, such as water maze and fear conditioning tests, could be of great importance in indentifying behavioral deficits in Ts65Dn mice and other transgenic mice models of neurocognitive disorders. Interestingly, after adding the satellite box, a completely novel environment to the Intellicage, Ts65Dn mice entered this new compartment sooner than 2N mice. These results highlight the lack of neophobia in these mice which could potentially be used as a behavioral assay for anxiety.

Spontaneous alternation in the Y- and T-maze was used for testing of spatial working memory in Ts65Dn mice. It has been shown that spontaneous alternation is a highly hippocampal-dependent task (Johnson et al., 1977; Gerlai, 1998) and animals with hippocampal lesions have decreased spatial memory (Devenport et al., 1988). Ts65Dn mice demonstrated significant deficit in spontaneous alternation in both T- and Y-maze tests. This result is in line with previous reports showing the deficit in spontaneous alternation at 3-4 months of age (Belichenko et al., 2007; Fernandez et al., 2007). Taken together, the impairment of Ts65Dn mice in spatial working memory and spontaneous alternation could be used as a robust assay for screening compounds affecting learning and memory. Similar to spontaneous alternation, DMP water maze tasks are highly hippocampal-dependent tasks (Steele and Morris, 1999). In our study, both male and female Ts65Dn mice showed deficits in this task. Each day 2N mice learn the spatial location of the hidden platform, and with each successive trial they find the platform in significantly shorter time compared to the Ts65Dn. It has been previously shown that Ts65Dn mice are impaired in hidden platform tasks of the Morris water maze (Sago et al., 2000) and have significant deficits in spatial working memory in the radial arm maze (Hunter et al., 2003). The DMP water maze task presented in this study can be used as a robust cognitive assay for testing spatial reference memory.

Both male and female Ts65Dn mice showed no deficit in the acquisition phase of the fear conditioning test. Ts65Dn mice did not display a significant deficit in tone-cued testing but did demonstrate a significant deficit in contextual testing, a hippocampus-dependent task (Kim and Fanselow, 1992). The hippocampus is highly involved in CFC but not in auditory conditioning (Anagnostaras et al., 1999). Male Ts65Dn mice have been shown to have difficulty learning the context discrimination task, which has similarities to the fear conditioning test (Hyde et al., 2001a), as well as retrieval of CFC using a different protocol (Costa et al., 2008). Ts65Dn mice did not display significant deficits in sensorimotor tasks, and they also have normal visual reflexes and olfactory function (Klein et al., 1996). Since the sensitivity of Ts65Dn mice to electrical shocks is normal (Hyde et al., 2001a), and the percentage of pre-tone freezing (baseline freezing) in Ts65Dn mice and 2N controls is almost the same, the difference between the percentage of freezing in contextual conditioning should be due to abnormalities in hippocampus-dependent context retrieval. In addition, the results of the startle response tests showed that both male and female Ts65Dn mice have no deficit in sensory-motor gating, and their reaction to the tones is similar to 2N mice.

Results from fear conditioning, DMP, Intellicage, and spontaneous alternation tests confirm that both male and female Ts65Dn mice have a robust deficit in hippocampus-dependent behavioral tasks, and that these tests are robust enough to be used for screening of therapeutic candidates. In addition, our results are in agreement with reported physiological abnormalities in the hippocampus of Ts65Dn mice, including reduced evoked LTP, which represents abnormal synaptic plasticity, reduced cAMP level, and morphological changes in dendrites (Dierssen et al., 1996; Siarey et al., 1997; Granholm et al., 2000; Kleschevnikov et al., 2004).

Social Behavior in Ts65Dn Mice

DS in children is associated with abnormal social behavior (Coe et al., 1999). Moreover, 10% of people suffering from DS also fulfill criteria for autism spectrum disorder (Dykens, 2007). In order to further investigate this phenomenon in a mouse model of DS, we tested the social memory and sociability of Ts65Dn mice.

The five-trial social memory experiments showed a deficit in social memory of the trisomic mice. In the first 30 seconds of the five trials, Ts65Dn mice exhibited the same level of interest in the familiar and novel intruder, whereas 2N mice showed a significant habituation response to the familiar OEF and a significant dishabituation response to the novel OEF. In contrast, in the final 30 seconds of the trials, both genotypes showed a significant habituation response. Habituation was also intact in both genotypes if mice were exposed to the urine of OEFs only. These findings suggest slower information processing of identity cues in Ts65Dn mice in a social context, but intact social memory if the identity cues are separated from a social context. We speculate that for Ts65Dn mice, identity recognition in a non-social context is less challenging than in a social context. This is reminiscent of a face recognition studies and deficit in children with DS (Wishart and Pitcairn, 2000). It has been shown that DS children performed normally in the relatively simple task of matching photographs of simultaneously presented faces, but performed significantly worse in the more challenging task of matching faces to non-present people. Moreover, children with DS showed increased recognition latency when the photographs of the faces were rotated 90 or 180 degrees (Wishart and Pitcairn, 2000).

In summary, our results demonstrate that Ts65Dn mice display a robust social memory deficit, while displaying normal habituation and dishabituation to social and non-social olfactory cues. In addition, Ts65Dn not showed no deficit in the social novelty test where the novel social contacts were presented with no delay to the subject mice. This further suggests that the deficit observed in social memory is selective and dependent on time between trials.

Pharmacological Experiments

It has been shown that the locus coeruleus (LC) and noradrenergic (NE) system via interaction with $\beta_1$-ADR, plays an Important role in hippocampal-mediated memory retrieval in fear conditioning (Murchison et al., 2004). The LC is the major source of norepinephrine in the brain and has neuronal projections to different areas of the brain, including the hippocampus and frontal cortex (Loughlin et al., 1986). We have also recently shown a significant degeneration of the LC in Ts65Dn mice and art increase in the $\beta_1$-ADR immunoreactivity in the hippocampus (Salehi et al., 2009). In addition, we have shown that restoration of norepinephrine level using L-DOPS in Ts65Dn mice restores this hippocampal-mediated contextual deficit in fear conditioning as well as nesting behavior (Salehi et al, 2009). In order to study if these effects are selectively and exclusively mediated via $\beta_1$-ADR, we used selective $\beta_1$-ADR agonist xamoterol, and $\beta_1$-ADR antagonist betaxolol, in CFC, T-maze, novel object recognition and locomotor activity in novel environment. Our results show that xamoterol can completely rescue the impaired learning and memory of Ts65Dn mice in CFC, novel object recognition, as well as spontaneous alternation. These effects were effectively and completely reversed by a $\beta_1$ adrenergic antagonist, betaxolol. Interestingly, $\beta_1$ receptor agonist does not have any effect on the hyperactivity observed in our experimental animals, and possibly restores the hippocampal-mediated function in the treated group selectively. These results suggest that the hippocampal-related behavioral deficit observed in the Ts65Dn is fully mediated by a decreased $\beta_1$ receptor signaling in hippocampus, and a selective activation of this receptor could be used as therapeutic approach for treatment of DS in man.

Tables 1 and 2 referred to above are shown below:

TABLE 1

Summary of Behavioral Experiments

| Behavioral Experiment | Task | Parameter studied | Brain region involved (Not Limited to) | Reference(s) |
|---|---|---|---|---|
| Activity and Motor Function | Activity Chamber | General motor activity in novel environment | Cerebellum, Cerebral cortex, Septum, Striatum, Thalamic reticular nucleus, Spinal cord, Hippocampus | (Deacon et al., 2002; Viggiano 2008) |
| | Phenotyper | General motor activity in home cage condition | Hippocampus, Prefrontal Cortex, Striatum, cerebral cortex, Cerebellum, Brain stem, Spinal cord | (Takakusaki, 2008) |
| | CatWalk | Gait Analysis | Striatum, Cerebral cortex, Cerebellum, Brain stem, Spinal cord | (Takakusaki, 2008) |
| Learning and Memory | T-maze Spontaneous Alternation Y-maze Spontaneous Alternation | Spatial working memory | Hippocampus | (Davenport et al., 1998; Gerlai, 1998; Johnson et al., 1977) |
| | Place learning in Intellicage | Spatial learning and memory retrieval in home cage condition | Hippocampus | (Galsworthy et al., 2005) |
| | Place Avoidance in Intellicage | Spatial learning and memory retrieval in home cage condition | Hippocampus, amygdala | (Galsworthy et al., 2005) |
| | Satellite box exploration in Intellicage | Exploratory of novel environment in home cage condition | Hippocampus | (Galsworthy et al., 2005) |
| | DMP Water Maze | Spatial working/episodic-like memory | Hippocampus | (Steele and Morris, 1999) |
| | Contextual and tone-cued Fear Conditioning | Pavlovian (associative) learning | Hippocampus and amygdala | (Anagnostaras et al., 1999; Kim and Fanselow, 1992) |

TABLE 1-continued

Summary of Behavioral Experiments

| Behavioral Experiment | Task | Parameter studied | Brain region involved (Not Limited to) | Reference(s) |
|---|---|---|---|---|
| Social Interaction | Sociability in 3-Chambered test | Sociability | Amygdala and prefrontal Cortex | (Lim and Young, 2006; Young et al., 2005) |
| | Social Novelty in 3-Chambered test | Social novelty | | |
| | 2-Trial Social memory in home cage | Social memory | Medial amygdala and lateral septum | |
| | 5-Trial Social Memort | Social memory | | |

TABLE 2

Results of Activity and Learning and memory tests

| Behavioral Parameter | Group | | 2N Mean ± SEM | Ts65Dn Mean ± SEM | p Value* | interpretation |
|---|---|---|---|---|---|---|
| Total Ambulatory Distance Moved in Activity Chamber (cm) | Female | | 2111 ± 225 | 3862 ± 594 | p < 0.01 | Ts65Dn mice are hyperactive in novel environment. Xamoterole has no effect on activity of the mice |
| | Male | No Treatment | 2264 ± 151 | 3638 ± 388 | p < 0.05 | |
| | | Saline | 2287 ± 253 | 3168 ± 163 | ns for treatment | |
| | | Xam | 2554 ± 192 | 3878 ± 765 | | |
| Total Vertical count in Activity Chamber (n) | Female | | 68.9 ± 13.8 | 145.2 ± 27.8 | p < 0.01 | Ts65Dn mice rear and jump more than 2N mice in novel environment |
| | Male | | 75.0 ± 6.1 | 147.7 ± 7.3 | p < 0.01 | |
| Baseline Distance Moved in Each Hour in PhenoTyper (cm) | Female | Dark | 2031 ± 508 | 4122 ± 789 | p < 0.05 | Ts65Dn mice are hyperactive in their home cage condition |
| | | Light | 532 ± 100 | 908 ± 205 | ns | |
| | Male | Dark | 1088 ± 196 | 2358 ± 350 | p < 0.01 | |
| | | Light | 366 ± 27 | 511 ± 96 | ns | |
| Distance Moved in the Running Wheel in PhenoTyper (cm) | Female | Dark | 27663 ± 8845 | 39204 ± 7842 | ns | Ts65Dn mice are hyperactive in the running wheel in their home cage condition |
| | | Light | 2298 ± 1207 | 1812 ± 971 | ns | |
| | Male | Dark | 16711 ± 6912 | 43645 ± 8032 | p < 0.05 | |
| | | Light | 634 ± 211 | 1762 ± 750 | ns | |
| Baseline Velocity in the PhenoTyper (cm/s) | Female | Dark | 7.32 ± 0.71 | 8.65 ± 0.89 | ns | Ts65Dn mice move faster in their home cage condition |
| | | Light | 8.66 ± 0.78 | 10.97 ± 0.70 | p < 0.06 | |
| | Male | Dark | 6.57 ± 0.56 | 7.23 ± 0.66 | ns | |
| | | Light | 7.87 ± 0.37 | 11.07 ± 1.02 | p < 0.05 | |
| Velocity in Running Wheel in PhenoTyper (cm/s) | Female | Dark | 23.16 ± 5.75 | 28.02 ± 4.23 | ns | Ts65Dn mice run faster in the running wheel in their home cage condition |
| | | Light | 17.22 ± 5.14 | 15.22 ± 4.48 | ns | |
| | Male | Dark | 10.90 ± 3.12 | 30.33 ± 4.36 | p < 0.01 | |
| | | Light | 4.15 ± 0.55 | 11.80 ± 2.48 | p < 0.05 | |
| Timer in Shelter in Each Hour During the Baseline Recording in PhenoTyper (s) | Female | Dark | 2653 ± 107 | 1630 ± 138 | p < 0.01 | Ts65Dn mice spend less amount of time in the shelter during the dark cycle |
| | | Light | 3238 ± 42 | 3145 ± 84 | ns | |
| | Male | Dark | 2536 ± 182 | 1591 ± 298 | p < 0.01 | |
| | | Light | 3177 ± 47 | 2752 ± 331 | ns | |
| Timer in Shelter in Each Hour During the Running Wheel in PhenoTyper (s) | Female | Dark | 1492 ± 256 | 665 ± 252 | p < 0.05 | Ts65Dn mice spend less amount of time in the shelter after adding the running wheel |
| | | Light | 3204 ± 56 | 1568 ± 578 | p < 0.05 | |
| | Male | Dark | 2025 ± 156 | 1440 ± 144 | p < 0.05 | |
| | | Light | 3189 ± 63 | 3271 ± 52 | ns | |
| % of Spontaneous Alternation in T-maze | Female | | 65.0 ± 3.3 | 48.5 ± 3.7 | p < 0.01 | Ts65Dn mice have impaired spatial working memory Xamoterole can rescue the deficit in spatial working memory and betaxolol prevents this effect |
| | Male | No Treatment | 72.2 ± 2.7 | 43.3 ± 5.0 | p < 0.001 | |
| | | Saline | 63.3 ± 4.0 | 41.9 ± 2.7 | p < 0.01 | |
| | | Xam | 64.4 ± 2.1 | 60.4 ± 4.5 | ns | |
| | | Xam + Betax | 66.7 ± 4.2 | 46.3 ± 2.8 | p < 0.01 | |
| % of Correct Visit in Probe Trial after Piece Learning in Intellicage | Female | | 60.3 ± 2.7 | 66.2 ± 4.0 | p < 0.270 | Ts65Dn mice don't show place learning deficit in stress free condition |
| % of visit to previously punished corner in intellicage | Female | | 5.3 ± 1.0 | 13.4 ± 3.4 | p < 0.05 | Ts65Dn mice show spatial learning deficit in stressful condition |
| Latency of First Satellite Box Entry in Intellicage (s) | Female | | 1172 ± 175 | 587 ± 75 | p < 0.005 | Ts65Dn mice enter into the new compartment sooner |
| Escape Latency in DMP Water Maze (s) | Female | T3 | 50.97 ± 6.80 | 76.42 ± 3.16 | p < 0.01 | Ts65Dn mice have deficit in spatial working memory/episodic like memory |
| | Male | T2 | 55.98 ± 5.18 | 77.29 ± 4.18 | p < 0.05 | |
| | | T3 | 46.50 ± 5.04 | 73.96 ± 4.64 | p < 0.01 | |
| | | T4 | 38.59 ± 5.50 | 70.44 ± 5.86 | p < 0.01 | |
| % of Total Investigation in Novel Object Recognition | Male | Saline | 59.0 ± 5.5 | 44.9 ± 3.3 | p < 0.05 | Xamoterol can rescue the impairment of novel object recoginition in Ts65Dn mice |
| | | Xam | 78.6 ± 2.6 | 73.6 ± 4.2 | ns | |
| % Freezing in Tone-cued Fear Conditioning | Female | | 27.19 ± 6.34 | 22.24 ± 3.98 | ns | Ts65Dn don't have deficit in tone cued fear conditioning |
| | Male | | 31.06 ± 3.84 | 21.73 ± 2.89 | ns | |
| % Freshing in Tone-cued Fear Conditioning | Female | | 16.37 ± 5.30 | 4.65 ± 1.66 | p < 0.05 | Ts65Dn mice show deficit in contextual fear conditioning Xamoterole rescues the deficit in |
| | Male | No Treatment | 19.33 ± 4.16 | 7.93 ± 2.87 | p < 0.05 | |
| | | Saline | 40.98 ± 6.25 | 19.65 ± 3.68 | p < 0.01 | |

TABLE 2-continued

Results of Activity and Learning and memory tests

| Behavioral Parameter | Group | 2N Mean ± SEM | Ts65Dn Mean ± SEM | p Value* | interpretation |
|---|---|---|---|---|---|
| | Xam | 38.43 ± 8.26 | 45.36 ± 12.40 | ns | contextual fear conditioning and |
| | Xam + Betax | 38.16 ± 4.07 | 21.51 ± 6.15 | p < 0.05 | betaxolol prevents this effect | ns: non significant,
Xam: xamoterole Batax betaxolo

Thus, the robust behavioral phenotyping platform used as described above, with both novel and standard behavioral assays, can be used for behavioral phenotyping of transgenic mice and pharmacological screening of compounds in mice models of DS and other neurodegenerative disorders. However, the present invention also provides methods for enhancing learning or memory or both in a mammal or for reducing memory in a mammal. Generally, compounds that are $\beta_1$-ADR agonists are used in accordance with the present invention to enhance learning or memory in a mammal, whereas compounds that are $\beta_1$-ADR antagonists are used in accordance with the present invention to reduce memory in a mammal.

The velocity of ambulatory movement in Ts65Dn mice in the exploratory activity in novel environment test was not significantly different from their control littermates, but the velocity of male mice was lower than female mice (effect of genotype, $F_{1, 36}=0.085$, p=0.772; effect of sex, $F_{1, 36}=13.54$, p=0.0008). Ts65Dn mice had lower resting time compared to the control mice (FIG. 10B: effect of genotype, $F_{1, 36}=11.96$, p=0.0014; effect of sex, $F_{1, 36}=0.177$, p=0.677).

In the Phenotyper experiment, females spent more time in the running wheel zone than males, and all subjects spent more time in the running wheel during the dark cycle than the light cycle (for effect of sex, $F_{1, 64}=8.21$, p=0.006; effect of cycle, $F_{1, 64}=55.48$, p<0.0001; effect of genotype, $F_{1, 64}=2.19$, p=0.145). All subjects spent more time in the water zone (drinking zone) during the dark cycle, and Ts65Dn mice spent more time in the water zone than 2N mice during the baseline period, but there is no significant effect of sex in this parameter (effect of genotype, $F_{1, 64}=7.44$, p=0.009; effect of cycle, $F_{1, 64}=54.25$, p<0.0001, effect of sex, $F_{1, 64}=0.06$, p=0.812). After adding a running wheel to the home cage, similar to the baseline period, all subjects spent more time in the water zone during the dark cycle than the light cycle, and Ts65Dn mice spent more time than 2N mice, but there is no significant effect of sex (effect of genotype, $F_{1, 64}=5.55$, p=0.022; effect of cycle, $F_{1, 64}=68.85$, p<0.0001, effect of sex, $F_{1, 64}=1.68$, p=0.20). All subjects spent more time in the food zone during the dark cycle, and Ts65Dn mice spent more time than 2N mice during the baseline period, but there is no significant effect of sex in this parameter (effect of genotype, $F_{1, 64}=16.53$, p<0.0001; effect of cycle, $F_{1, 64}=109.47$, p<0.0001, effect of sex, $F_{1, 64}=0.48$, p=0.493). After adding a running wheel to the home cage, mice spent more time in the food zone during the dark cycle, Ts65Dn mice spent more time than 2N mice, and male mice spent more time than female mice in the food zone (effect of genotype, $F_{1, 64}=9.63$, p=0.003; effect of cycle, $F_{1, 64}=83.71$, p<0.0001, effect of sex, $F_{1, 64}=24.28$, p<0.0001).

In the CatWalk test, the intensity of the front paw print in Ts65Dn mice is lower than in the 2N mice and lower in males than females (effect of genotype, $F_{1, 38}=11.17$, p=0.002; effect of sex, $F_{1, 38}=42.97$, p=0.0001). Similar results were found in hind paw intensity (effect of genotype, $F_{1, 38}=12.99$, p=0.0009; effect of sex, $F_{1, 38}=18.21$, p=0.0001). There was no significant difference in the regularity index between Ts65Dn and 2N mice or between male and female mice (effect of genotype, $F_{1, 38}=2.25$, p=0.142; effect of sex, $F_{1, 38}=2.95$, p=0.094). To analyze the step pattern, an inter-limb coordination parameter, percentage of Ab pattern during trials was analyzed. There was no significant difference in percentage of Ab step pattern between Ts65Dn and 2N mice, but the Ab pattern in males was lower than females (effect of Genotype, $F_{1, 38}=0.47$, p=0.497; effect of sex, $F_{1, 38}=9.42$, p=0.004). There was no significant difference between Ts65Dn and 2N mice in front paws base of support, or the distance between the center of the right and left paw, but the front paw base of support in male mice was larger than females (effect of sex, $F_{1, 38}=8.23$, p=0.007). Similarly, Ts65Dn and 2N mice did not show significant difference in hind paw base of support but, female mice showed significantly higher hind paw base of support than males (effect of genotype, $F_{1, 38}=0.28$, p=0.598; effect of sex, $F_{1, 38}=34.47$, p=0.0001). There was no significant difference in stride length of the front paw between Ts65Dn and 2N mice and between male and female mice (effect of genotype, $F_{1, 38}=2.03$, p=0.163; effect of sex, $F_{1, 38}=1.93$, p=0.172). Stride length of the hind paw in Ts65Dn mice was longer than 2N controls, but sex had no effect on this parameter (effect of genotype, $F_{1, 38}=5.57$, p=0.024; effect of sex, $F_{1, 38}=1.74$, p=0.195). Front paw swing speed was not significantly different in Ts65Dn mice compared to 2N controls, but front paw swing speed was lower in male than in female mice (effect of genotype, $F_{1, 38}=2.20$, p=0.146; effect of sex, $F_{1, 38}=8.36$, p=0.006). Similar results were seen in hind paw swing speed (effect of genotype, $F_{1, 38}=0.41$, p=0.526; effect of sex, $F_{1, 38}=10.74$, p=0.002).

In the water maze visible platform experiment, both female and male Ts65Dn mice showed no significant difference in velocity of swimming compared to 2N controls (effect of genotype in female, $F_{1, 42}=1.79$, p=0.21, and in male $F_{1, 42}=0.88$, p=0.36).

In the 3-chamber test, during a 10 min "habituation" session both Ts65Dn and 2N mice did not exhibit a side preference for the left or right chamber (effect of left or right, $F_{1, 18}=0.55$, p=0.467). In the "sociability" session, animals spent significantly more time in the chamber containing the stranger mouse than the chamber containing the empty cage (effect of genotype, $F_{1,18}=0.334$, p=0.571; effect of object, $F_{1,18}=101.3$, p<0.0001). During the "social novelty" session, animals spent more time in the chamber containing the stranger than in the chamber containing the familiar mouse (effect of genotype, $F_{1, 18}=0.207$, p=0.655; effect of object, $F_{1,18}=33.79$, p<0.0001). Analysis of the final 30-seconds revealed a significant habituation, response for both genotypes, a significant dishabituation for 2N, and non-significant dishabituation trend for Ts65Dn mice (effect of genotype, $F_{1, 68}=0.011$, p=0.919; effect of trial, $F_{4, 68}=11.22$, p=0.0001).

Enhancement of Learning and Memory

It is explicitly contemplated that one or more $\beta_1$-ADR agonists, partial agonists or ligands or salts thereof may be used in accordance with the present invention to enhance learning and memory in mammals. The mammals may be mammals used for experimental purposes, such as mice, rats, cats, dogs or pigs; or humans for clinical treatment purposes. Further, while the present invention may be used to improve learning and memory in mammals suffering from diseases and conditions that have resulted in impaired learning or memory or both, the present invention may be used to improve learning or memory or both in mammals having a normal baseline of learning or memory or both. While it is not required that the $\beta_1$-ADR agonists used for this aspect of the present invention be selective $\beta_1$-ADR agonists, it is preferred that they be. Examplary compounds are xamoterol, noradrenalin, isoprenaline, dopamine and/or dobutamine and the pharmaceutically-acceptable salts thereof, such as phosphate, sulfate, chloride, acetate or citrate. Generally, these compounds or salts thereof are administered by injection, such as intravenous or intramuscular. Amounts used are from about 0.1 to 10 mg per kg of mammalian body weight, however more or less may be used at the discretion of the treating physician or investigator.

Reducing Memory

It is also explicitly contemplated that one or more $\beta_1$-ADR antagonists or salts thereof may be used in accordance with the present invention to reduce memory in mammals. The mammals may be used for experimental purposes, such as mice, rats, cats, dogs or pigs; or humans for clinical treatment purposes. This aspect of the present invention may be advantageous in treating post-traumatic stress disorder reducing memories which may trigger further episodes. Exemplary compounds include aryloxypropanolamines such as acebutolol, atenolol, betaxolol, esmolol, metoprolol, and bisoprolol and the pharmaceutically-acceptable salts thereof, such as the phosphate, sulfate, chloride, acetate or citrate. Generally, these compounds or salts thereof are administered by injection, such as intravenous or intramuscular. Amounts used are from about 0.1 to 10 mg per kg of mammalian body weight, however more or less may be used at the discretion of the treating physician or investigator.

Additionally, as noted above, it is explicitly contemplated to use not only selective agonists, but also partial agonists as well as ligands for the receptor to accomplish the enhancement of learning and memory.

Finally, it is also explicitly contemplated to regulate the function of the receptor for enhancing learning and memory by regulating signal cascades both upstream and/or downstream of the receptor.

What is claimed is:

1. A method for treating a human having Alzheimer's disease, the method comprising administering to a human in need thereof an effective amount of xamoterol or one or more pharmacologically-acceptable salts of xamoterol to improve spatial working memory of said human.

2. The method of claim 1, wherein said spatial working memory is improved by agonist stimulation of β1-adrenoreceptors.

3. The method of claim 1, wherein xamoterol is administered.

4. The method of claim 1, wherein one or more salts of xamoterol are administered.

5. The method of claim 1, wherein a mixture of xamoterol and one or more salts are administered.

6. The method of claim 1, wherein the xamoterol and/or one or more salts is administered orally.

7. The method of claim 1, wherein the xamoterol and/or one or more salts is administered by injection.

8. The method of claim 7, wherein the injection is intravenous.

9. The method of claim 7, wherein the injection is intramuscular.

10. The method of claim 4, wherein the one or more salts are acid addition salts with an organic acid.

11. The method of claim 4, wherein the one or more salts are acid addition salts with an inorganic acid.

12. The method of claim 1, wherein the xamoterol and/or one or more salts thereof is administered in an amount of about 0.1 to 10 mg/kg of body weight.

* * * * *